(12) United States Patent
Brennan et al.

(10) Patent No.: US 9,706,790 B2
(45) Date of Patent: **\*Jul. 18, 2017**

(54) COMPOUNDS, COMPOSITIONS, AND METHODS FOR REDUCING OR ELIMINATING BITTER TASTE

(75) Inventors: Francis Xavier Brennan, Philadelphia, PA (US); William P. Jones, Skokie, IL (US); Jane V. Leland, Wilmette, IL (US); David Hayashi, Chicago, IL (US)

(73) Assignee: CHROMOCELL CORPORATION, North Brunswick, NJ (US)

( * ) Notice: Subject to any disclaimer, the term of this patent is extended or adjusted under 35 U.S.C. 154(b) by 63 days.

This patent is subject to a terminal disclaimer.

(21) Appl. No.: 14/352,632

(22) PCT Filed: Oct. 20, 2011

(86) PCT No.: PCT/US2011/057146
§ 371 (c)(1),
(2), (4) Date: Jul. 31, 2014

(87) PCT Pub. No.: WO2013/058758
PCT Pub. Date: Apr. 25, 2013

(65) Prior Publication Data
US 2014/0377381 A1    Dec. 25, 2014

(51) Int. Cl.
| | | |
|---|---|---|
| *A23L 29/00* | (2016.01) | |
| *A23L 27/30* | (2016.01) | |
| *A23L 33/00* | (2016.01) | |
| *A23L 27/40* | (2016.01) | |
| *A23L 27/00* | (2016.01) | |
| *A23L 13/00* | (2016.01) | |
| *A23L 5/20* | (2016.01) | |
| *A23L 1/22* | (2006.01) | |

(52) U.S. Cl.
CPC ........... *A23L 1/22083* (2013.01); *A23L 27/40* (2016.08); *A23L 27/86* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 2,492,588 A | 12/1949 | Marhofer | |
| 3,919,318 A | 11/1975 | Acton et al. | |
| 4,187,863 A | 2/1980 | Kovats et al. | |
| 4,347,858 A | 9/1982 | Klemarczyk | |
| 4,788,220 A * | 11/1988 | Mody | A61K 31/19 514/557 |
| 4,983,394 A | 1/1991 | Hussein et al. | |
| 5,602,184 A | 2/1997 | Myers et al. | |
| 5,643,941 A | 7/1997 | Kurtz et al. | |
| 5,719,180 A | 2/1998 | Shudo et al. | |
| 5,958,496 A | 9/1999 | Amino et al. | |
| 6,020,505 A | 2/2000 | Hirose et al. | |
| 7,576,049 B2 | 8/2009 | Shaath et al. | |
| 8,865,779 B2 | 10/2014 | Shekdar | |
| 9,408,407 B2 | 8/2016 | Shekdar et al. | |
| 2003/0228402 A1 | 12/2003 | Franklin et al. | |
| 2005/0158329 A1 | 7/2005 | Ghosh | |
| 2006/0257543 A1 | 11/2006 | Tachdjian | |
| 2007/0077300 A1* | 4/2007 | Wynn | A61K 9/0056 424/472 |
| 2008/0317923 A1 | 12/2008 | Ley | |
| 2009/0035337 A1 | 2/2009 | Artiga-Gonzalez et al. | |
| 2009/0035444 A1 | 2/2009 | Salemme et al. | |
| 2009/0041917 A1 | 2/2009 | Salemme et al. | |
| 2010/0035340 A1 | 2/2010 | Drayna et al. | |
| 2010/0056621 A1 | 3/2010 | Behrens et al. | |
| 2010/0184796 A1 | 7/2010 | Behrens et al. | |
| 2010/0215740 A1* | 8/2010 | Pilgaonkar | A61K 9/0056 424/465 |
| 2011/0045069 A1 | 2/2011 | Ley et al. | |
| 2013/0096209 A1 | 4/2013 | Hayashi | |
| 2015/0237900 A1 | 8/2015 | Shekdar | |
| 2017/0000178 A1 | 1/2017 | Shekdar et al. | |

FOREIGN PATENT DOCUMENTS

| | | | |
|---|---|---|---|
| CN | 1559558 A | 1/2005 | |
| CN | 1572755 | 2/2005 | |
| CN | 1857426 A | 11/2006 | |
| CN | 1947697 A | 4/2007 | |
| CN | 101234072 A | 8/2008 | |
| CN | 101249051 A | 8/2008 | |
| DE | WO 9802182 A1 * | 1/1998 | ............ A61K 45/06 |

(Continued)

OTHER PUBLICATIONS

Ana Lúcia A. Vendramini and Luiz C. Trugo. Phenolic Compounds in Acerola Fruit (*Malpighia punicifolia*, L.). J. Braz. Chem. Soc., vol. 15, No. 5, 664-668, 2004.*
Definition of "pharmaceutically active ingredient" from the Free Dictionary online, downloaded May 23, 2016, from: http://medical-dictionary.thefreedictionary.com/Active+pharmaceutical+ingredients.*
Jorge A. Pino and Rolando Marbot. Volatile Flavor Constituents of Acerola (*Malpighia emarginata* DC.) Fruit. J. Agric. Food Chem. 2001, 49, 5880-5882.*
J. V. Formica and W. Regelson. Review of the Biology of Quercetin and Related Bioflavonoids.Fd Chem. Toxic.. vol. 33, No. 12, pp. 1061-1080, 1995.*
Arun et al., "Evaluation of hot melt coating as taste masking tool," International Research Journal of Pharmacy, 2(8):169-172 (2011).
Brown et al., "Diet and Refsun's Disease: The determination of phytanic acid and phytol in certain foods and the application of this knowledge to the choice of suitable convenience food for patients with Refsum's Disease," Journal of Human Nutrition and Dietetics, 6(4):295-305 (1993).

(Continued)

*Primary Examiner* — Frederick Krass
*Assistant Examiner* — Michael P Cohen
(74) *Attorney, Agent, or Firm* — Sabine U Epelbaum; Marcus C Sands; Ropes & Gray LLP

(57) ABSTRACT

The present invention provides edible compositions comprising a compound of the present invention, food products comprising such edible compositions and methods of preparing such food products. The present invention also provides methods of reducing the amount of NaCl in a food product, methods of reducing the sodium intake in a diet, and methods of reducing bitter taste in a food product.

7 Claims, 1 Drawing Sheet

(56) References Cited

FOREIGN PATENT DOCUMENTS

| | | |
|---|---|---|
| EP | 0821055 | 1/1998 |
| EP | 0941671 | 9/1999 |
| EP | 1321140 A1 | 6/2003 |
| EP | 2198859 | 6/2010 |
| EP | 2305048 | 4/2011 |
| EP | 2324833 | 5/2011 |
| GB | 809015 | 2/1959 |
| JP | 44004651 | 2/1968 |
| JP | H08268851 A | 10/1996 |
| JP | 11060503 | 3/1999 |
| JP | 11221042 | 8/1999 |
| JP | 2001039922 A | 2/2001 |
| JP | 2003073282 | 3/2003 |
| JP | 2004018431 | 1/2004 |
| JP | 2005013138 | 1/2005 |
| JP | 2005015686 | 1/2005 |
| JP | 2005082594 | 3/2005 |
| JP | 2005187360 | 7/2005 |
| JP | 2006025706 | 2/2006 |
| JP | 2007002005 | 1/2007 |
| JP | 2009517063 | 4/2009 |
| JP | 2011115149 | 6/2011 |
| WO | WO-9310677 | 6/1993 |
| WO | WO9420080 | 9/1994 |
| WO | WO9704666 | 2/1997 |
| WO | WO-0036933 | 6/2000 |
| WO | WO-03031385 | 4/2003 |
| WO | WO-2004029087 | 4/2004 |
| WO | WO-2004087096 | 10/2004 |
| WO | WO-2006087991 | 8/2006 |
| WO | WO-2006101807 | 9/2006 |
| WO | WO-2008119196 | 10/2008 |
| WO | WO-2008119197 | 10/2008 |
| WO | WO-2009015504 | 2/2009 |
| WO | WO-2009112800 | 9/2009 |
| WO | WO-2009137838 | 11/2009 |
| WO | WO-2009140784 | 11/2009 |
| WO | WO-2010023874 | 3/2010 |
| WO | WO-2011130705 | 10/2011 |

OTHER PUBLICATIONS

Pezoa et al., "Development of a Formulation of Sustained Release Potassium Chloride," Drug Development and Industrial Pharmacy, 17(13):1875-1882 (1991).
Amazon Camphor, downloaded http://www.amazon.com/Camphor-Tablets-Premium-Alcamphor-Sanvall/dp/B006T6O3UC/ref=sr_1_sc_2?ie=UTF8&qid=1444914178&sr=8-2-spell &keywords=champor+block (2005) (1 page).
Bayer Low Dose Aspirin, downloaded http://www.drugstore.com/ bayer-low-dose-aspirin-pain-reliever-81mg-enteric-coated-tablets/ qxp168632?catid=183122 (2005) (1 page).
eBay Borneal, downloaded http://www.ebay.com/itm/Borneol-99-5-predominantly-endo-for-synthesis-10g-/ 271832546600?hash=item3f4a7b7d28 (2005) (1 page).
Papas et al., "Composition for Treating Inflammatory Bowel Disease," CAS, 142:349067 (2005) (2 pages).
Sigma-Aldrich Myrtenolm, downloaded http://www.sigmaaldrich. com/catalog/product/aldrich/188417?lang=en&region=US (2005) (3 pages).
Sigma-Aldrich Myrtenyl Acetate, downloaded from http://www. sigmaaldrich.com/catalog/product/aldrich/w376507?lang=en &region=US (2005) (4 pages).
Sigma-Aldrich Pinene, downloaded from http://www.sigmaaldrich. com/catalog/product/aldrich/147524?lang=en&region=US (2005) (4 pages).
Sigma-Aldrich Pinocarveol, downloaded from http://www. sigmaaldrich.com/catalog/product/aldrich/80613?lang=en &region=US (2005) (3 pages).
Sigma-Aldrich Verbenone, downloaded from http://www. sigmaaldrich.com/catalog/product/aldrich/218251?lang=en &region=US&utm_term=-verbenone&utm_medium=cpc&utm_ source=bing&utm_campaign=Aldrich%20Position %20Support%20Global%20(Bing%20ebizpfs) (2005) (4 pages).
AlsoSalt Salt Substitute 2 pages, www.alsosalt.com, downloaded Jan. 31, 2011.
Bauer et al., "Common Fragrance and Flavor Materials: Preparation and Uses," Fourth Edition, Wiley-VCH Verlag GmbH, pp. 1-282 (2001).
Behrens et al., Structural Requirements for Bitter Taste Receptor Activation, AChemS 2009 Annual Meeting, Sarasota, FL, Poster P141, Apr. 22-26, 2009.
Brockhoff et al., "Structural Requirements of Bitter Taste Receptor Activation," PNAS, 107(24): 11110-11115 (2010).
Doyle et al., "Sodium Reduction and Its Effect on Food Safety, Food Quality, and Human Health," Comprehensive Reviews in Food Science and Food Safety, 9(1):44-56 (2009).
Kuhn et al., "Bitter taste receptors for saccharin and acesulfame K," Journal of Neuroscience, 24(45):10260-10265 (2004).
Kumar et al., "Formulation Evaluation of Mouth Dissolving Tablets of Fenofibrate Using Sublimation Technique," International Journal of ChemTech Research, 1(4):840-850 (2009).
Maguire, "Reducing Salt in SA Food," Web publication, pp. 1-2 (2007) http://www.developtechnology.co.za/index2.php?option= com_content&do_pdf=1&id=19926.
Slack et al., "Inhibition of Bitter Taste Receptors," AChemS 2009 Annual Meeting, Sarasota, FL, Poster P195, Apr. 22-26, 2009.
Slack et al., "Modulation of Bitter Taste Perception by a Small Molecule hTAS2R Antagonist," Curr Biol., 20(12): 1104-1109 (2010).
The Good Scents Company Information Systems (available at www.thegoodscentscompany.com, accessed Mar. 16, 2011).
Winnig et al., "Saccharin: Artificial Sweetener, Bitter Tastant, and Sweet Taste Inhibitor," Sweetness and Sweeteners, Chapter 16, pp. 230-240 Chapter DOI: 10.1021/bk-2008-0979.ch016 ACS Symposium Series, vol. 979 http://pubs.acs.org/doi/abs/10.1021/bk-2008-0979.ch016.
Winnig et al., "Saccharin: Artificial Sweetener, Bitter Tastant, and Sweet Taste Inhibitor," the 231st ACS National Meeting Spring, 2006, poster AGFD 111, Atlanta, GA Mar. 26-30, 2006.
Atawia et al., "Effect of freezing of jasmine flowers on their jasmine concrete and absolute qualities", Egyptian Journal of Food Science, 16(1-2):237-247 (1989).
Bezman et al., "Differential Effects of Tomato (*Lycopersicon esculentum* Mill) Matrix on the Volatility of Important Aroma Compounds," Journal of Agricultural and Food Chemistry, 51(3):722-726 (2003).
Lilic et al., "Possibility of replacement of sodium chloride by potassium chloride in cooked sausages—sensory characteristics and health aspects," Biotechnology in Animal Husbandry, 24(1-2):133-138 (2008).
Marais,"Terpenes in the Aroma of Grapes and Wines: A Review," South African Journal of Enology and Viticulture, 4(2):49-58 (1983).
Potassium: Tips for People with Chronic Kidney Disease (CKD), US Department of Health and Human Services, National Institutes of Health & National Kidney Disease Education Program, NIH Publication No. 11-7407, Revised Sep. 2011 [online], <URL: http:// nkdep.nih.gov/resources/nutrition-potassium-508.pdf> (2 pages).
http://www.colawp.com/colas/400/cola467_recipe.html.
Adam et al., "Clues to early diagenetic sulfurization processes from mild chemical cleavage of labile sulfur-rich geomacromolecules," Geochimica et Cosmochimica Acta, 64(20):3485-3503 (2000).
Bang et al., "Phytol, SSADH inhibitory diterpenoid of Lactuca sativa," Archives of Pharmacal Research, 25(5):643-646 (2002).
Hebting et al., "Biomarker evidence for a major preservation pathway of sedimentary organic carbon," Science, 312(5780):1627-1631 (2006).
Kim et al., "Terpene and Phenolic Constituents of Lactuca indica," Archives of Pharmacal Research, 31(8):983-988 (2008).
Lee et al., "Phytochemical Constituens of Cirsium setidens Nakai and Their Cytotoxicity against Human Cancer Cell Lines," Archives in Pharmacal Research, 25(5):628-635 (2002).

(56) References Cited

OTHER PUBLICATIONS

Rodriguez-Garcia et al., "Evaluation of the antioxidant activity of three microalgal species for use as dietary supplements and in the preservation of foods," Food Chemistry, 108(3):1023-1026 (2008).
Senatore et al., "Chemical Composition of the Essential Oil from Aerial Parts of *Stachys palustris* L. (Lamiaceae) Growing Wild in Southern Italy," Croatica Chemica Acta, 80(1):135-139 (2007).
Stevenson et al., "Resistance to extinction of conditioned odor perceptions: evaluative conditioning is not unique," Journal of Experimental Psychology: Learning, Memory and Cognition, 26(2):423-40 (2000).
Trost et al., "Taste + odor interactions in compound aversion conditioning," Learning and Behavior, 32(4):440-453 (2004).

\* cited by examiner

| Compound No. | Conc. Of KCl in Marinade (Conc. of KCl in Solid Turkey) | Conc. of Compound Tested in ppm (# of panelists discerning decrease in bitter taste/# of panelists tested) | Conc. at Which At Least 50% of Panelists Discerned Decrease in Bitter Taste (ppm) | Conc. at Which At Least 50% of Panelists Discerned Decrease in Bitter Taste and $p \leq 0.1$ (ppm) |
|---|---|---|---|---|
| 5 | 10.9% (1.6%) | 0.1 (36/69)<br>1 (35/69)<br>10 (48/69)<br>20 (32/69) | 0.1<br>1<br>10 | 10 |
| 6 | 10.9% (1.6%) | 0.1 (33/69)<br>1 (42/69)<br>10 (34/69)<br>20 (36/69) | 1<br>20 | 1 |
| 7 | 10.9% (1.6%) | 0.1 (32/63)<br>1 (40/63)<br>10 (28/63)<br>20 (24/63) | 0.1<br>1 | 1 |
| 8 | 10.9% (1.6%) | 0.1 (46/78)<br>1 (37/78)<br>10 (47/78)<br>20 (42/78) | 10<br>20 | 10 |
| Standard | 10.9% (1.6%) | -- | -- | -- |

COMPOUNDS, COMPOSITIONS, AND METHODS FOR REDUCING OR ELIMINATING BITTER TASTE

CROSS REFERENCE TO RELATED APPLICATIONS

This application is the National Phase entry under 35 USC §371 of PCT/US2011/057146, filed Oct. 20, 2011, the contents of which are hereby incorporated by reference in its entirety.

FIELD OF THE INVENTION

The present invention relates to flavor in edible compositions.

BACKGROUND OF THE INVENTION

The sense of taste. e.g., in human, can detect at least five traditional tastes: sweet, sour, salty, bitter, and umami (savory). Many nutritious substances including vegetables, foods, food ingredients and nutrients comprise bitter tastants and/or have a bitter taste. In addition, many pharmaceutical substances important to maintain or improve health comprise bitter tastants and/or have a bitter taste. While certain food products and consumer products have desirable bitter tastes, including coffee, beer and dark chocolate, in many contexts, consumers dislike such bitter tastes. For example, many consumers dislike the perception of certain bitter tastants and/or bitter taste and will avoid food or pharmaceutical products with an undesirable bitter tastant or bitter taste in favor of food and pharmaceutical products that have reduced levels of undesirable bitter tastants or that have reduced or that completely lack bitter taste. This aversion to products containing undesirable bitter tastants and/or having undesirable bitter taste may be caused by perception of bitter tastants and/or bitter taste mediated by activation of bitter receptors present in the oral cavity and/or in the gastrointestinal tract. In many cases, consumer dislike of bitter tastants and/or bitter taste prevents or hampers improvement of the nutritive quality and safety of foods as desired levels of nutrients or preservatives comprising bitter tastants and/or having bitter taste cannot be used. Also, dislike of or aversion to the bitter tastants or bitter taste of some pharmaceutical agents negatively impacts compliance with prescribed regimens for their use.

For instance, several additives, preservatives, emulsifiers and foodstuffs used in the production of food products comprise bitter tastants and/or have a bitter taste. While these additives, preservatives, emulsifiers and foodstuffs may affect the taste of a food product, they may also be important for improving the shelf life, nutritive quality, or texture of the food product. For example, the increasing trend of hypertension and cardiovascular disease has been attributed, in part, to the high sodium intake of the Western diet. Accordingly, substitution of sodium chloride with another salty tasting compound is desirable. The most common sodium chloride substitute is potassium chloride, which, to a portion of the population, is perceived as possessing a bitter taste in addition to its salty taste. The bitter taste of potassium chloride limits the extent to which it may be used to replace sodium chloride in foods without causing undesired bitter taste for the portion of the population sensitive to it.

Another common food additive, sodium lactate, has a broad antimicrobial action, is effective at inhibiting spoilage, and growth of pathogenic bacteria, and is commonly used in food products (e.g., meat and poultry products) to extend shelf life and increase food safety. Due to its sodium content, however, sodium lactate, can be undesirable as a preservative. Potassium lactate, which has similar antimicrobial properties, has been used in lieu of sodium lactate. However, potassium lactate is also associated with a bitter taste which limits the extent to which it may be used to replace sodium lactate in foods without causing undesired bitter taste.

In addition, the increasing incidence of obesity and diabetes has been attributed, in part, to the high sugar intake of many diets. Accordingly, substitution of sugar with another sweet tasting compound is desirable. Artificial and natural sugar substitutes that may be used to reduce sugar in foods are often associated with bitter taste which again limit the extent to which these may be used to replace sugar in foods without causing adverse bitter taste. For example, a common sugar substitute is Acesulfame K, which also has a bitter taste in addition to its sweet taste.

Without being limited by theory, bitter, sweet, and umami tastants and compounds typically elicit a taste response via G-protein coupled receptors, while salty and sour tastants and compounds are typically hypothesized to elicit a taste response via ion channels. Bitter taste receptors belong to the T2R (also referred to as TAS2R) family of G-protein coupled receptors that induce intracellular calcium concentration changes in response to a bitter tastant. T2R receptors act via gustducin, a taste-specific G-protein. There are at least twenty-five different members of the T2R family, suggesting that the perception of bitter taste is complex, involving several different tastant-receptor interactions. Compounds capable of modulating the activation and/or signaling of bitter taste receptors in the oral cavity and/or the gastrointestinal tract could be effective to allow desired usage levels of bitter tastants or bitter tasting substances in food and pharmaceutical products without resulting in consumer dislike of such products due to perception of the increased levels of bitter tastants or bitter tastes. In some instances, blockers or modulators of bitter taste receptors and bitter taste may reduce the perception of bitter tastants and/or bitter taste via the bitter taste receptors and/or taste transduction signaling machinery present in the oral cavity and/or the gastrointestinal tract.

Traditionally in food preparation and pharmaceuticals, bitter taste was masked using sweeteners and other tastants, including salt. In some cases, however, this is undesirable or insufficient because it can alter, mask, or interfere with other tastes/flavors/impressions (e.g., non bitter tastes or desired bitter tastes) in the food product. Additionally, this approach has rarely been able to completely mask the bitter taste present in such food products or pharmaceuticals. For that reason, compounds which reduce bitter taste instead of, or in addition to, masking agents are preferred.

It is, therefore, desirable to provide compounds that may be added to food products, consumer products and pharmaceuticals comprising bitter tastants or having a bitter taste to eliminate, modulate or reduce the perception of the bitter tastants or bitter taste or to reduce the corresponding activation of the bitter receptors in the oral cavity and/or the gastrointestinal tract. Similarly, it is desirable to provide food products, consumer products, and pharmaceutical compositions comprising such compounds. It is also desirable to decrease the sodium intake of a subject using such compounds to eliminate, modulate or reduce the perception of bitter taste associated with salt substitutes. It is further desirable to decrease the sugar intake of a subject using such compounds to eliminate, modulate or reduce the perception of bitter taste associated with sugar substitutes.

SUMMARY OF THE INVENTION

The present invention provides compounds that modulate bitter taste, edible compositions comprising such compounds, and methods of preparing such edible compositions. The present invention also provides methods of reducing the amount of sodium or sugar in an edible composition and methods of reducing bitter taste of an edible composition. The present invention further provides a method of reducing, modulating or eliminating the bitter taste of a food, consumer or pharmaceutical product in a subject. The present invention also provides a method of modulating, particularly reducing the activation of a bitter taste receptor.

Edible Compositions

One aspect of the present invention provides edible compositions for reducing bitter taste of a bitter tastant. In some embodiments, the edible composition comprises a branched alkene compound. In some embodiments, the branched alkene compound is a compound having a molecular weight less than about 1000, 500, or 300 daltons. In certain embodiments, the branched alkene compound is a compound of Formula (I), or Compounds 1-5 or a comestibly or biologically acceptable salt or derivative thereof, or an enantiomer or diastereomer thereof.

In certain embodiments, the compound of Formula (I) is phytol or a comestibly or biologically acceptable salt or derivative thereof, or an enantiomer or diastereomer thereof.

In some embodiments, the edible composition comprises a cyclohexadiene-based compound. In some embodiments, the cyclohexadiene-based compound is a compound having a molecular weight less than about 1000, 500, or 300 daltons. In certain embodiments, the cyclohexadiene-based compound is a compound of Formula (II), or Compound 6 or a comestibly or biologically acceptable salt or derivative thereof, or an enantiomer or diastereomer thereof.

In certain embodiments, the compound of Formula (II) is damascenone or a comestibly or biologically acceptable salt or derivative thereof, or an enantiomer or diastereomer thereof.

In some embodiments, the edible composition comprises a branched alkene ester compound. In some embodiments, the branched alkene ester compound is a compound having a molecular weight less than about 1000, 500, or 300 daltons. In certain embodiments, the branched alkene ester compound is a compound of Formula (III), or Compound 7 or a comestibly or biologically acceptable salt or derivative thereof, or an enantiomer or diastereomer thereof.

In certain embodiments, the compound of Formula (III) is citronellyl tiglate or a comestibly or biologically acceptable salt or derivative thereof, or an enantiomer or diastereomer thereof.

In some embodiments, the edible composition comprises a benzodioxole-based compound. In some embodiments, the benzodioxole-based compound is a compound having a molecular weight less than about 1000, 500, or 300 daltons. In certain embodiments, the benzodioxole-based compound is a compound of Formula (IV), or Compound 8 or a comestibly or biologically acceptable salt or derivative thereof, or an enantiomer or diastereomer thereof.

In certain embodiments, the compound of Formula (IV) is 2-Methyl-3-(3,4-methylenedioxyphenyl)-propanal or a comestibly or biologically acceptable salt or derivative thereof, or an enantiomer or diastereomer thereof.

In some embodiments, the edible composition comprises (a) a compound of the invention; and (b) a bitter tastant. In some embodiments, the compound of the invention is a compound having a molecular weight less than about 1000, 500, or 300 daltons. In certain embodiments, the compound of the invention is a compound of Formula (I), Formula (II), Formula (III), or Formula (IV), as described herein, or combinations thereof.

In another embodiment, the edible composition comprises (a) any one of Compounds 1-8, as described herein, or combinations thereof; and (b) a bitter tastant.

According to the invention, the bitter tastant can be inherent in, e.g., a food product (such as coffee or chocolate) or can be a component of an edible composition (such as a bitter tasting preservative). In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant is a potassium salt. In some embodiments, the bitter tastant present in the edible compositions is KCl. In other embodiments, the bitter tastant present in the edible composition is potassium lactate.

In some embodiments, the edible composition further comprises a sodium salt. In some embodiments, the edible composition further comprises NaCl. In other embodiments, the edible composition further comprises sodium lactate. In some embodiments, the edible composition further comprises sugar.

In another aspect of the invention, the edible composition is a food product comprising at least one compound of the invention. In certain embodiments, the compound of the invention is a compound of Formula (I), Formula (II), Formula (III), or Formula (IV), as described herein, or combinations thereof. In another embodiment, the compound of the invention is any one of Compounds 1-8, as described herein, or combinations thereof.

In another aspect of the present invention, the edible composition is a pharmaceutical composition comprising a bitter tasting pharmaceutically active ingredient and a compound of Formula (I), Formula (II), Formula (III), or Formula (IV), as described herein, or combinations thereof. In some embodiments, the pharmaceutical composition comprises a bitter tasting pharmaceutically active ingredient and any one of Compounds 1-8, as described herein, or combinations thereof.

In yet other embodiments, the edible composition is a pharmaceutical composition comprising a pharmaceutically active ingredient, a bitter tastant, and a compound of Formula (I), Formula (II), Formula (III), or Formula (IV), as described herein, or combinations thereof. In yet other embodiments, the pharmaceutical composition comprises a pharmaceutically active ingredient, a bitter tastant, and any one of Compounds 1-8, as described herein, or combinations thereof.

In another aspect of the present invention, the edible composition is a consumer product comprising a bitter tastant and a compound of Formula (I), Formula (II), Formula (III), or Formula (IV), as described herein, or combinations thereof. In other embodiments, the consumer product comprises a bitter tastant and any one of Compounds 1-8, as described herein, or combinations thereof.

Yet another embodiment of the present invention provides a consumer product for reducing bitter taste of a bitter tastant, wherein said consumer product comprises a compound of Formula (I), Formula (II), Formula (III), or Formula (IV), as described herein, or combinations thereof. In yet other embodiments, the consumer product for reducing bitter taste of a bitter tastant comprises any one of Compounds 1-8, as described herein, or combinations thereof.

In a further aspect, the present invention provides a method of preparing an edible composition comprising:
(a) providing a comestibly acceptable carrier; and
(b) adding to the comestibly acceptable carrier of (a) a compound of Formula (I), Formula (II), Formula (III), or Formula (IV), as described herein, or combinations thereof.

In another embodiment, the method of preparing an edible composition comprises:
(a) providing a comestibly acceptable carrier; and
(b) adding to the comestibly acceptable carrier of (a) any one of Compounds 1-8, as described herein, or combinations thereof.

In some embodiments, the edible composition is a food product, a consumer product or a pharmaceutical composition. In some embodiments, the comestibly acceptable carrier is a foodstuff, a food product, or a pharmaceutically acceptable carrier.

In some embodiments, the comestibly acceptable carrier in (a) is inherently bitter. In such embodiments, the comestibly acceptable carrier may inherently contain a bitter tastant (i.e., the comestibly acceptable carrier is bitter without addition of a bitter tastant). In some embodiments, the inherent bitter tastant is a bitter tasting salt. In some embodiments, the inherently bitter foodstuff comprises a potassium salt, a magnesium salt, or a calcium salt. In some embodiments, the inherently bitter foodstuff comprises a potassium salt, such as KCl.

In other embodiments, the method of preparing an edible composition further comprises: (c) adding a bitter tastant. In some embodiments, the bitter tastant used in the methods of preparing an edible composition is a bitter tasting salt. In some embodiments, the bitter tastant used in the methods of preparing an edible composition is a potassium salt, a magnesium salt, or a calcium salt. In some embodiments, the bitter tastant used in the methods of preparing an edible composition is a potassium salt. In some embodiments, the bitter tastant used in the methods of preparing an edible composition is KCl. In other embodiments, the bitter tastant used in the methods of preparing an edible composition is potassium lactate.

In some embodiments, the edible composition further comprises a sodium salt. In some embodiments, the edible composition further comprises NaCl. In some embodiments, the edible composition further comprises sodium lactate. In some embodiments, the edible composition further comprises sugar.

The present invention also provides a method of reducing the amount of sodium in an edible composition. In some embodiments, such methods comprise:
(a) replacing an amount of one or more sodium salts used in preparing an edible composition with an amount of one or more potassium salts; and
(b) incorporating into the edible composition an effective amount of a compound according to Formula (I), Formula (II), Formula (III), or Formula (IV), as described herein, or combinations thereof.

In another embodiment, the method of reducing the amount of sodium in an edible composition comprises:
(a) replacing an amount of one or more sodium salts used in preparing an edible composition with an amount of one or more potassium salts; and
(b) incorporating into the edible composition an effective amount of any one of Compounds 1-8, as described herein, or combinations thereof.

In some embodiments, the edible composition is a food product, a consumer product or a pharmaceutical composition.

In some embodiments of the present invention, the method of reducing the amount of sodium in an edible composition comprises incorporating into the edible composition an amount of the compound sufficient to permit replacement of up to 25% of the sodium present in an edible composition with potassium. In other embodiments, the amount of the compound incorporated into the edible composition is sufficient to permit replacement of up to 50% of the sodium present in an edible composition with potassium. In yet other embodiments, the amount of the compound incorporated into the edible composition is sufficient to permit replacement of up to 75% of the sodium present in an edible composition with potassium. In other embodiments, the amount of the compound incorporated into the edible composition is sufficient to permit replacement of up to 100% of the sodium present in an edible composition with potassium. In some embodiments, the edible composition maintains a salty flavor.

The present invention also provides a method of reducing the amount of NaCl in an edible composition. In some embodiments, such methods comprise:
(a) replacing an amount of NaCl used in preparing an edible composition with an amount of KCl; and
(b) incorporating into the edible composition an effective amount of a compound according to Formula (I), Formula (II), Formula (III), or Formula (IV), as described herein, or combinations thereof.

In another embodiment, the method of reducing the amount of NaCl in an edible composition comprises:
(a) replacing an amount of NaCl used in preparing an edible composition with an amount of KCl; and
(b) incorporating into the edible composition an effective amount of any one of Compounds 1-8, as described herein, or combinations thereof.

In some embodiments of the present invention, the method of reducing the amount of sodium in an edible composition comprises incorporating into the edible composition an amount of the compound sufficient to permit replacement of up to 25% of the NaCl present in an edible composition with KCl. In other embodiments, the amount of the compound incorporated into the edible composition is sufficient to permit replacement of up to 50% of the NaCl present in an edible composition with KCl. In yet other embodiments, the amount of the compound incorporated into the edible composition is sufficient to permit replacement of up to 75% of the NaCl present in an edible composition with KCl. In other embodiments, the amount of the compound incorporated into the edible composition is sufficient to permit replacement of up to 100% of the NaCl present in an edible composition with KCl. In some embodiments, the edible composition maintains a salty flavor.

In another embodiment, the present invention provides a method of reducing the amount of sodium lactate in an edible composition comprises:
(a) replacing an amount of sodium lactate used in preparing an edible composition with an amount of potassium lactate; and
(b) incorporating into the edible composition an effective amount of a compound according to Formula (I), Formula (II), Formula (III), or Formula (IV), as described herein, or combinations thereof.

In another embodiment, the invention provides a method of reducing the amount of sodium lactate in an edible composition comprising:
(a) replacing an amount of sodium lactate used in preparing an edible composition with an amount of potassium lactate; and
(b) incorporating into the edible composition an effective amount of any one of Compounds 1-8, as described herein, or combinations thereof.

In some embodiments, the edible composition is a food product, a consumer product or a pharmaceutical composition.

In some embodiments of the present invention, the method of reducing the amount of sodium lactate in an edible composition comprises incorporating into the edible composition an amount of the compound sufficient to permit replacement of up to 25% of the sodium lactate present in an edible composition with potassium lactate. In other embodiments, the amount of the compound incorporated into the edible composition is sufficient to permit replacement of up to 50% of the sodium lactate present in an edible composition with potassium lactate. In yet other embodiments, the amount of the compound incorporated into the edible composition is sufficient to permit replacement of up to 75% of the sodium lactate present in an edible composition with potassium lactate. In other embodiments, the amount of the compound incorporated into the edible composition is sufficient to permit replacement of up to 100% of the sodium lactate present in an edible composition with potassium lactate. In some embodiments, the edible composition has the same shelf life as an edible composition comprising sodium lactate.

In another embodiment, the invention provides a method of reducing the amount of sugar in an edible composition comprising:
(a) replacing an amount of sugar used in preparing an edible composition with an amount of Acesulfame K; and
(b) incorporating into the edible composition an effective amount of a compound according to Formula (I), Formula (II), Formula (III), or Formula (IV), as described herein, or combinations thereof.

In another embodiment, the invention provides a method of reducing the amount of sugar in an edible composition comprising:
(a) replacing an amount of sugar used in preparing an edible composition with an amount of Acesulfame K; and
(b) incorporating into the edible composition an effective amount of any one of Compounds 1-8, as described herein, or combinations thereof.

In some embodiments, the edible composition is a food product, a consumer product or a pharmaceutical composition.

In some embodiments of the present invention, the method of reducing the amount of sugar in an edible composition comprises incorporating into the edible composition an amount of the compound sufficient to permit replacement of up to 25% of the sugar present in an edible composition with Acesulfame K. In other embodiments, the amount of the compound incorporated into the edible composition is sufficient to permit replacement of up to 50% of the sugar present in an edible composition with Acesulfame K. In yet other embodiments, the amount of the compound incorporated into the edible composition is sufficient to permit replacement of up to 75% of the sugar present in an edible composition with Acesulfame K. In other embodiments, the amount of the compound incorporated into the edible composition is sufficient to permit replacement of up to 100% of the sugar present in an edible composition with Acesulfame K. In some embodiments, the edible composition maintains a sweet flavor.

The present invention also provides a method of reducing the sodium intake of a subject. Such method comprises:
(a) replacing an amount of NaCl used in preparing an edible composition with an amount of KCl; and
(b) incorporating into the edible composition an effective amount of a compound according to Formula (I), Formula (II), Formula (III), or Formula (IV), as described herein, or combinations thereof, thereby reducing the sodium intake of the subject.

In another embodiment, the method of reducing the sodium intake of a subject comprises:
(a) replacing an amount of NaCl used in preparing an edible composition with an amount of KCl; and
(b) incorporating into the edible composition an effective amount of any one of Compounds 1-8, as described herein, or combinations thereof, thereby reducing the sodium intake of the subject.

In another embodiment, the method of reducing the sodium intake of a subject comprises:
(a) replacing an amount of sodium lactate used in preparing an edible composition with an amount of potassium lactate; and
(b) incorporating into the edible composition an effective amount of a compound according to Formula (I), Formula (II), Formula (III), or Formula (IV), as described herein, or combinations thereof, thereby reducing the sodium intake of the subject.

In another embodiment, the method of reducing the sodium intake of a subject comprises:
(a) replacing an amount of sodium lactate used in preparing an edible composition with an amount of potassium lactate; and
(b) incorporating into the edible composition an effective amount of any one of Compounds 1-8, as described herein, or combinations thereof, thereby reducing the sodium intake of the subject.

In some embodiments, the edible composition is a food product, a consumer product or a pharmaceutical composition.

In some embodiments of the present invention, the methods of reducing the sodium intake of a subject further comprise (c) identifying a subject in need thereof. In some embodiments, the methods of reducing the sodium intake of a subject comprise incorporating into the edible composition an amount of the compound sufficient to reduce sodium intake by up to 25% using potassium replacement. In other embodiments, the amount of compound added in (b) is sufficient to reduce sodium intake by up to 50% using potassium replacement. In yet other embodiments, the amount of compound added in (b) is sufficient to reduce sodium intake by up to 75% using potassium replacement. In other embodiments, the amount of compound added in (b) is sufficient to reduce sodium intake by up to 100% using potassium replacement.

The present invention also provides a method of reducing sugar intake of a subject comprising:
(a) replacing an amount of sugar used in preparing an edible composition with an amount of Acesulfame K; and
(b) incorporating into the edible composition an effective amount of a compound according to Formula (I), Formula (II), Formula (III), as described herein, or combinations thereof, thereby reducing the sugar intake of the subject.

In another embodiment, the method of reducing the sugar intake of a subject comprises:
(a) replacing an amount of sugar used in preparing an edible composition with an amount of Acesulfame K; and
(b) incorporating into the edible composition an effective amount of any one of Compounds 1-8, as described herein, or combinations thereof, thereby reducing the sugar intake of the subject.

In some embodiments, the edible composition is a food product, a consumer product or a pharmaceutical composition.

In some embodiments of the present invention, the methods of reducing the sugar intake of a subject further comprise (c) identifying a subject in need thereof. In some embodiments, the methods of reducing the sugar intake of a subject comprise incorporating into the edible composition an amount of the compound sufficient to reduce sugar intake by up to 25% using Acesulfame K replacement. In other embodiments, the amount of compound added in (b) is sufficient to reduce sugar intake by up to 50% using Acesulfame K replacement. In yet other embodiments, the amount of compound added in (b) is sufficient to reduce sugar intake by up to 75% using Acesulfame K replacement. In other embodiments, the amount of compound added in (b) is sufficient to reduce sugar intake by up to 100% using Acesulfame K replacement.

The present invention also provides a method of reducing the bitter taste attributed to a bitter tastant in an edible composition comprising adding an effective amount of a compound according to Formula (I), Formula (II), Formula (III), or Formula (IV), as described herein, or combinations thereof, to the edible composition such that any bitter taste induced by the bitter tastant is reduced. In other embodiments, the compound added to the edible composition is any one of Compounds 1-8, as described herein, or combinations thereof.

The present invention further provides a method of reducing the bitter taste attributed to a bitter tastant in an edible composition comprising ingesting an effective amount of a compound according to Formula (I), Formula (II), Formula (III), or Formula (IV), as described herein, or combinations thereof, before, along with, or after the edible composition such that any bitter taste induced by the bitter tastant is reduced. In other embodiments, the compound ingested with the edible composition is any one of Compounds 1-8, as described herein, or combinations thereof.

In some embodiments, the edible composition is a food product, a consumer product or a pharmaceutical composition.

In some embodiments, the method reduces the bitter taste induced by the bitter tastant by up to 25%. In some embodiments, the method reduces the bitter taste induced by the bitter tastant by up to 50%. In other embodiments, the bitter taste induced by the bitter tastant is reduced by up to 75%. In yet other embodiments, the bitter taste induced by the bitter tastant is reduced by up to 100%. In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant present in the edible compositions is KCl.

In a further aspect, the present invention provides a method of preserving an edible composition comprising:

(a) providing an edible composition; and
(b) adding to the edible composition of (a) potassium lactate and an effective amount of a compound of Formula (I), Formula (II), Formula (III), or Formula (IV), as described herein, or combinations thereof.

In another embodiment, the method of preserving an edible composition comprises:
(a) providing an edible composition; and
(b) adding to the edible composition of (a) potassium lactate and an effective amount of any one of Compounds 1-8, as described herein, or combinations thereof.

The present invention also provides a method of reducing the amount of sodium in an edible composition while preserving the edible composition. In some embodiments, such method comprises:
(a) replacing an amount of sodium lactate used in preparing an edible composition with an amount of potassium lactate; and
(b) incorporating into the edible composition an effective amount of a compound according to Formula (I), Formula (II), Formula (III), or Formula (IV), as described herein, or combinations thereof.

The present invention also provides a method of reducing the amount of sodium in an edible composition while preserving the edible composition. In some embodiments, such method comprises:
(a) replacing an amount of sodium lactate used in preparing an edible composition with an amount of potassium lactate; and
(b) incorporating into the edible composition an effective amount of any one of Compounds 1-8, as described herein, or combinations thereof.

In some embodiments, the edible composition is a food product. In some embodiments, the edible composition is a consumer product. In some embodiments, the edible composition is a pharmaceutical composition.

The present invention also provides a method of reducing or eliminating bitter taste in a subject utilizing an edible composition comprising a compound of Formula (I), Formula (II). Formula (III), or Formula (IV), as described herein, or combinations thereof. In other embodiments, the composition that reduces or eliminates a bitter taste in a subject comprises any one of Compounds 1-8, as described herein, or combinations thereof.

In some embodiments the bitter taste is inherent. In some embodiments, the bitter taste is due to a bitter tasting salt. In some embodiments, the bitter taste is due to a potassium salt, a magnesium salt, or a calcium salt. In some embodiments, the bitter taste is due to KCl. In other embodiments, the bitter taste is due to potassium lactate.

The present invention also provides a method of inhibiting or reducing the activation and/or signaling of a bitter taste receptor, wherein the method comprises contacting a bitter taste receptor with a compound of Formula (I), Formula (II), Formula (III), or Formula (IV), as described herein, or combinations thereof. In other embodiments, the method comprises contacting a bitter taste receptor with any one of Compounds 1-8, as described herein, or combinations thereof. In some embodiments, the bitter taste receptor is in the oral cavity. In other embodiments, the bitter taste receptor is in the gastrointestinal tract, for example, in the stomach. In other embodiments, the bitter taste receptor is in an in vitro assay.

Particular embodiments of the invention are set forth in the following numbered paragraphs:

1. A composition comprising a compound according to Formula (I):

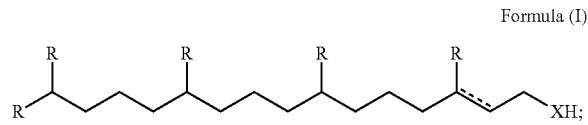

Formula (I)

or a comestibly or biologically acceptable salt or derivative thereof, or an enantiomer or diastereomer thereof,
wherein, as valence and stability permit:
X is S or O;
each R is independently H, $C_1$-$C_6$ alkyl, $C_2$-$C_6$ alkenyl, or $C_2$-$C_6$ alkynyl;
wherein the dotted bond indicates an optional carbon-carbon double bond; and
wherein the composition is edible and capable of reducing bitter taste of a bitter tastant.

2. The composition according to paragraph 1, wherein as valence and stability permit:
X is S or O;
each R is independently H, $C_1$-$C_3$ alkyl, $C_2$-$C_3$ alkenyl, or $C_2$-$C_3$ alkynyl; and
wherein the dotted bond indicates an optional carbon-carbon double bond.

3. The composition according to paragraph 1, wherein as valence and stability permit:
X is O;
each R is independently H, $C_1$-$C_3$ alkyl, $C_2$-$C_3$ alkenyl, or $C_2$-$C_3$ alkynyl; and
wherein the dotted bond indicates an optional carbon-carbon double bond.

4. The composition according to paragraph 1, wherein as valence and stability permit:
X is S or O;
each R is independently H or $C_1$-$C_3$ alkyl; and
wherein the dotted bond indicates an optional carbon-carbon double bond.

5. The composition according to paragraph 1, wherein as valence and stability permit:
X is O;
each R is independently H or $C_1$-$C_3$ alkyl; and
wherein the dotted bond indicates an optional carbon-carbon double bond.

6. The composition according to paragraph 1, wherein said compound according to Formula (I) is selected from:

Compound 1

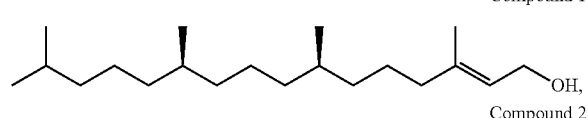

Compound 2

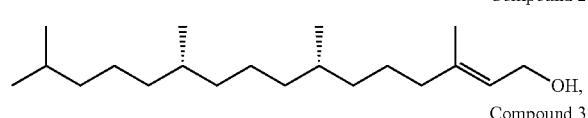

Compound 3

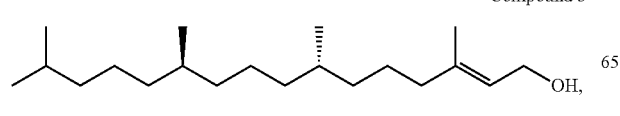

Compound 4

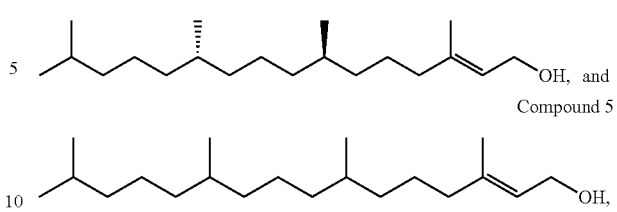

and

Compound 5

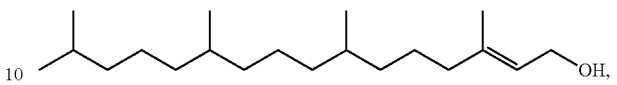

comestibly or biologically acceptable derivatives thereof, or an enantiomer or diastereomer thereof.

7. A composition comprising a compound according to Formula (II):

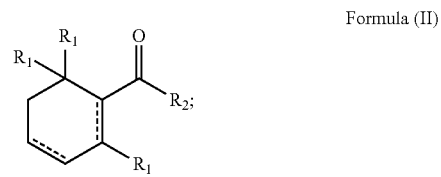

Formula (II)

or a comestibly or biologically acceptable salt or derivative thereof, or an enantiomer or diastereomer thereof,
wherein, as valence and stability permit:
each $R_1$ is independently H, $C_1$-$C_6$ alkyl, $C_2$-$C_6$ alkenyl, or $C_2$-$C_6$ alkynyl;
$R_2$ is H, $C_1$-$C_6$ alkyl, $C_2$-$C_6$ alkenyl, or $C_2$-$C_6$ alkynyl; and
the dotted bonds represent optional carbon-carbon double bonds;
wherein the composition is edible and capable of reducing bitter taste of a bitter tastant 8. The composition according to paragraph 7, wherein as valence and stability permit:
each $R_1$ is independently H, $C_1$-$C_3$ alkyl, $C_2$-$C_3$ alkenyl, or $C_2$-$C_3$ alkynyl;
$R_2$ is H, $C_1$-$C_3$ alkyl, $C_2$-$C_3$ alkenyl, or $C_2$-$C_3$ alkynyl; and
the dotted bonds represent optional carbon-carbon double bonds.

9. The composition according to paragraph 7, wherein as valence and stability permit:
each $R_1$ is independently H or $C_1$-$C_3$ alkyl;
$R_2$ is H, $C_1$-$C_3$ alkyl or $C_2$-$C_3$ alkenyl; and
the dotted bonds represent optional carbon-carbon double bonds.

10. The composition according to paragraph 7, wherein as valence and stability permit:
each $R_1$ is independently H or $C_1$-$C_3$ alkyl;
$R_2$ is H or $C_2$-$C_3$ alkenyl; and
the dotted bonds represent optional carbon-carbon double bonds.

11. The composition according to paragraph 7, wherein as valence and stability permit:
each $R_1$ is independently H or $C_1$-$C_3$ alkyl;
$R_2$ is H or $C_2$-$C_3$ alkenyl; and
each dotted line is a carbon-carbon double bond.

12. The composition according to paragraph 7, wherein said compound according to Formula (II) is selected from:

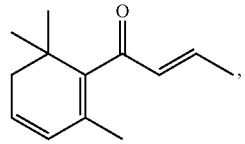

Compound 6 comestibly or biologically acceptable derivatives thereof, or an enantiomer or diastereomer thereof.

13. A composition comprising a compound according to Formula (III):

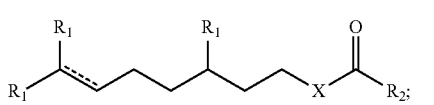

Formula (III)

or a comestibly or biologically acceptable salt or derivative thereof, or an enantiomer or diastereomer thereof,
wherein, as valence and stability permit:
X=S or O;
each $R_1$ is independently H, $C_1$-$C_6$ alkyl, $C_2$-$C_6$ alkenyl, or $C_2$-$C_6$ alkynyl;
$R_2$ is H, $C_1$-$C_{10}$ alkyl, $C_2$-$C_{10}$ alkenyl, or $C_2$-$C_{10}$ alkynyl; and
the dotted bond represents an optional carbon-carbon double bond;
wherein the composition is edible and capable of reducing bitter taste of a bitter tastant.

14. The composition according to paragraph 13, wherein as valence and stability permit:
X=S or O;
each $R_1$ is independently H, $C_1$-$C_6$ alkyl, $C_2$-$C_6$ alkenyl, or $C_2$-$C_6$ alkynyl;
$R_2$ is H, $C_1$-$C_6$ alkyl, $C_2$-$C_6$ alkenyl, or $C_2$-$C_6$ alkynyl; and
the dotted line represents an optional carbon-carbon double bond.

15. The composition according to paragraph 13, wherein as valence and stability permit:
X=S or O;
each $R_1$ is independently H, $C_1$-$C_3$ alkyl, $C_2$-$C_3$ alkenyl, or $C_2$-$C_3$ alkynyl;
$R_2$ is H, $C_1$-$C_6$ alkyl, $C_2$-$C_6$ alkenyl, or $C_2$-$C_6$ alkynyl; and
the dotted line represents an optional carbon-carbon double bond.

16. The composition according to paragraph 13, wherein as valence and stability permit:
X=O;
each $R_1$ is independently H, $C_1$-$C_3$ alkyl, $C_2$-$C_3$ alkenyl, or $C_2$-$C_3$ alkynyl;
$R_2$ is H, $C_1$-$C_6$ alkyl, $C_2$-$C_6$ alkenyl, or $C_2$-$C_6$ alkynyl; and
the dotted line represents an optional carbon-carbon double bond.

17. The composition according to paragraph 13, wherein as valence and stability permit:
X=S or O;
each $R_1$ is independently H, $C_1$-$C_3$ alkyl, $C_2$-$C_3$ alkenyl, or $C_2$-$C_3$ alkynyl;
$R_2$ is H, $C_1$-$C_4$ alkyl, $C_2$-$C_4$ alkenyl, or $C_2$-$C_4$ alkynyl; and
the dotted line represents an optional carbon-carbon double bond.

18. The composition according to paragraph 13, wherein as valence and stability permit:
X=O;
each $R_1$ is independently H, $C_1$-$C_3$ alkyl, $C_2$-$C_3$ alkenyl, or $C_2$-$C_3$ alkynyl;
$R_2$ is H, $C_1$-$C_4$ alkyl, $C_2$-$C_4$ alkenyl, or $C_2$-$C_4$ alkynyl; and
the dotted line represents an optional carbon-carbon double bond.

19. The composition according to paragraph 13, wherein as valence and stability permit:
X=O;
each $R_1$ is independently H, $C_1$-$C_3$ alkyl, $C_2$-$C_3$ alkenyl, or $C_2$-$C_3$ alkynyl;
$R_2$ is H, $C_1$-$C_4$ alkyl, $C_2$-$C_4$ alkenyl, or $C_2$-$C_4$ alkynyl; and
the dotted line is a carbon-carbon double bond.

20. The composition according to paragraph 13, wherein said compound according to Formula (III) is selected from:

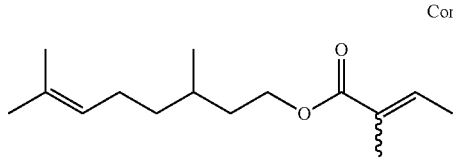

Compound 7 comestibly or biologically acceptable derivatives thereof, or an enantiomer or diastereomer thereof.

21. A composition comprising a compound according to Formula (IV):

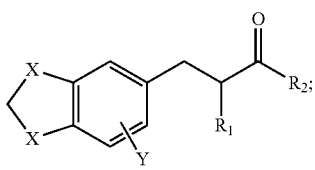

Formula (IV)

or a comestibly or biologically acceptable salt or derivative thereof, or an enantiomer or diastereomer thereof,
wherein, as valence and stability permit:
each X is independently S or O;
Y=H or halogen;
$R_1$ is H, $C_1$-$C_6$ alkyl, $C_2$-$C_6$ alkenyl, or $C_2$-$C_6$ alkynyl; and
$R_2$ is H, $C_1$-$C_6$ alkyl, $C_2$-$C_6$ alkenyl, or $C_2$-$C_6$ alkynyl;
wherein the composition is edible and capable of reducing bitter taste of a bitter tastant.

22. The composition according to paragraph 21, wherein as valence and stability permit:
each X is independently S or O;
Y=H or halogen;
$R_1$ is H, $C_1$-$C_3$ alkyl, $C_2$-$C_3$ alkenyl, or $C_2$-$C_3$ alkynyl; and
$R_2$ is H, $C_1$-$C_3$ alkyl, $C_2$-$C_3$ alkenyl, or $C_2$-$C_3$ alkynyl.

23. The composition according to paragraph 21, wherein as valence and stability permit:
each X is independently S or O;
Y=H or halogen;
$R_1$ is H, $C_1$-$C_3$ alkyl, $C_2$-$C_3$ alkenyl, or $C_2$-$C_3$ alkynyl; and
$R_2$ is H or $C_1$-$C_3$ alkyl.

24. The composition according to paragraph 21, wherein as valence and stability permit:
X=O;
Y=H;

$R_1$ is H, $C_1$-$C_3$ alkyl, $C_2$-$C_3$ alkenyl, or $C_2$-$C_3$ alkynyl; and
$R_2$ is H or $C_1$-$C_3$ alkyl.

25. The composition according to paragraph 21, wherein as valence and stability permit:
X=O;
Y=H;
$R_1$ is H or $C_1$-$C_3$ alkyl; and
$R_2$ is H or $C_1$-$C_3$ alkyl.

26. The composition according to paragraph 21, wherein as valence and stability permit:
X=O;
Y=H;
$R_1$ is H or $C_1$-$C_3$ alkyl; and
$R_2$ is H.

27. The composition according to paragraph 21, wherein said compound according to Formula (IV) is selected from:

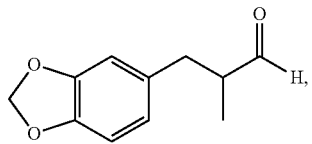

Compound 8 comestibly or biologically acceptable derivatives thereof, or an enantiomer or diastereomer thereof.

28. A composition comprising:
   (a) a compound according to Formula (I), Formula (II), Formula (III), or Formula (IV), as described herein, or combinations thereof, or any one of Compounds 1-8, as described herein, or combinations thereof; and
   (b) a bitter tastant,
   wherein the composition is edible.

29. The composition according to paragraph 28, wherein the bitter tastant is a foodstuff.

30. The composition according to paragraph 28, wherein the bitter tastant is a bitter tasting salt.

31. The composition according to paragraph 30, wherein the bitter tasting salt is a magnesium salt, a calcium salt, or a potassium salt.

32. The composition according to paragraph 31, wherein the potassium containing salt is KCl or potassium lactate.

33. The composition of any one of paragraphs 1-32, wherein the edible composition further comprises one or more components selected from the group consisting of: NaCl, sodium lactate, and sugar.

34. A food product comprising the compositions of any one of paragraphs 1-33.

35. A method of preparing an edible composition comprising:
   (a) providing a comestibly acceptable carrier; and
   (b) adding to the comestibly acceptable carrier of (a) a compound according to Formula (I), Formula (II), Formula (III), or Formula (IV), as described herein, or combinations thereof, or any one of Compounds 1-8, as described herein, or combinations thereof.

36. The method according to paragraph 35, wherein said comestibly acceptable carrier is inherently bitter.

37. The method according to paragraph 36, wherein the comestibly acceptable carrier comprises a bitter tasting salt.

38. The method according to paragraph 37, wherein the bitter tasting salt is a magnesium salt, a calcium salt, or a potassium salt.

39. The method according to paragraph 38, wherein the potassium salt is KCl or potassium lactate.

40. The method according to any one of paragraphs 35-39, wherein the edible composition further comprises one or more components selected from the group consisting of: NaCl, sodium lactate, and sugar.

41. The method according to paragraph 35, wherein the method further comprises:
   (c) adding a bitter tastant.

42. The method according to paragraph 41, wherein the bitter tastant is a bitter tasting salt.

43. The method according to paragraph 42, wherein the bitter tasting salt is a magnesium salt, a calcium salt, or a potassium salt.

44. The method according to paragraph 43, wherein the potassium salt is KCl or potassium lactate.

45. The method according to any one of paragraphs 41-44, wherein the edible composition further comprises one or more components selected from the group consisting of: NaCl, sodium lactate, and sugar.

46. A method of reducing the amount of NaCl in an edible composition comprising:
   (a) replacing an amount of NaCl used in preparing an edible composition with an amount of KCl; and
   (b) incorporating into the edible composition an effective amount of a compound according to Formula (I), Formula (II), Formula (III), or Formula (IV), as described herein, or combinations thereof, or any one of Compounds 1-8, as described herein, or combinations thereof.

47. The method according to paragraph 46, wherein the amount of compound added in (b) is sufficient to permit replacement of the amount of NaCl typically present in the edible composition by up to 25%.

48. The method according to paragraph 46, wherein the amount of compound added in (b) is sufficient to permit replacement of the amount of NaCl typically present in the edible composition by up to 50%.

49. The method according to paragraph 46, wherein the amount of compound added in (b) is sufficient to permit replacement of the amount of NaCl typically present in the edible composition by up to 75%.

50. The method according to paragraph 46, wherein the amount of compound added in (b) is sufficient to permit replacement of the amount of NaCl typically present in the edible composition by up to 100%.

51. The method according to any one of paragraphs 46-50, wherein the edible composition maintains a salty flavor.

52. A method of reducing the amount of sodium lactate in an edible composition comprising:
   (a) replacing an amount of sodium lactate used in preparing an edible composition with an amount of potassium lactate; and
   (b) incorporating into the edible composition an effective amount of a compound according to Formula (I), Formula (II), Formula (III), or Formula (IV), as described herein, or combinations thereof, or any one of Compounds 1-8, as described herein, or combinations thereof as described herein, or combinations thereof.

53. The method according to paragraph 52, wherein the amount of compound added in (b) is sufficient to permit replacement of the amount of sodium lactate typically present in the edible composition by up to 25%.

54. The method according to paragraph 52, wherein the amount of compound added in (b) is sufficient to permit replacement of the amount of sodium lactate typically present in the edible composition by up to 50%.

55. The method according to paragraph 52, wherein the amount of compound added in (b) is sufficient to permit replacement of the amount of sodium lactate typically present in the edible composition by up to 75%.

56. The method according to paragraph 52, wherein the amount of compound added in (b) is sufficient to permit replacement of the amount of sodium lactate typically present in the edible composition by up to 100%.

57. The method according to any one of paragraphs 52-56, wherein the edible composition has the same shelf life as an edible composition comprising sodium lactate.

58. A method of reducing the amount of sugar in an edible composition comprising:
    (a) replacing an amount of sugar present an edible composition with an amount of Acesulfame K; and
    (b) incorporating into the edible composition an effective amount of a compound according to Formula (I), Formula (II), Formula (III), or Formula (IV), as described herein, or combinations thereof, or any one of Compounds 1-8, as described herein, or combinations thereof.

59. The method according to paragraph 58, wherein the amount of compound added in (b) is sufficient to permit replacement of the amount of sugar typically present in the edible composition by up to 25%.

60. The method according to paragraph 58, wherein the amount of compound added in (b) is sufficient to permit replacement of the amount of sugar typically present in the edible composition by up to 50%.

61. The method according to paragraph 58, wherein the amount of compound added in (b) is sufficient to permit replacement of the amount of sugar typically present in the edible composition by up to 75%.

62. The method according to paragraph 58, wherein the amount of compound added in (b) is sufficient to permit replacement of the amount of sugar typically present in the edible composition by up to 100%.

63. The method according to any one of paragraphs 58-62, wherein the edible composition maintains a sweet flavor.

64. A method of reducing the sodium intake of a subject, the method comprising:
    (a) replacing an amount of a sodium salt used in preparing an edible composition with an amount of a potassium salt; and
    (b) incorporating into the edible composition an effective amount of a compound according to Formula (I), Formula (II), Formula (III), or Formula (IV), as described herein, or combinations thereof, or any one of Compounds 1-8, as described herein, or combinations thereof.

65. The method according to paragraph 64, wherein the sodium salt is NaCl and the potassium salt is KCl.

66. The method according to paragraph 64, wherein the sodium salt is sodium lactate, and the potassium salt is potassium lactate.

67. The method according to any one of paragraphs 64-66, wherein the method further comprises (c) identifying a subject in need thereof.

68. The method according to any one of paragraphs 64-67, wherein the amount of compound added in (b) is sufficient to reduce sodium intake by up to 25% by replacement with potassium.

69. The method according to any one of paragraphs 64-67, wherein the amount of compound added in (b) is sufficient to reduce sodium intake by up to 50% by replacement with potassium.

70. The method according to any one of paragraphs 64-67, wherein the amount of compound added in (b) is sufficient to reduce sodium intake by up to 75% by replacement with potassium.

71. The method according to any one of paragraphs 64-67, wherein the amount of compound added in (b) is sufficient to reduce sodium intake by up to 100% by replacement with potassium.

72. A method of reducing the sugar intake of a subject, the method comprising:
    (a) replacing an amount of sugar used in preparing an edible composition with an amount of a Acesulfame K; and
    (b) incorporating into the edible composition an effective amount of a compound according to Formula (I), Formula (II), Formula (III), or Formula (IV), as described herein, or combinations thereof, or any one of Compounds 1-8, as described herein, or combinations thereof.

73. The method according to paragraph 72, wherein the method further comprises (c) identifying a subject in need thereof.

74. The method according to paragraph 72 or 73, wherein the amount of compound added in (b) is sufficient to reduce sugar intake by up to 25% by replacement with Acesulfame K.

75. The method according to paragraph 72 or 73, wherein the amount of compound added in (b) is sufficient to reduce sugar intake by up to 50% by replacement with Acesulfame K.

76. The method according to paragraph 72 or 73, wherein the amount of compound added in (b) is sufficient to reduce sugar intake by up to 75% by replacement with Acesulfame K.

77. The method according to paragraph 72 or 73, wherein the amount of compound added in (b) is sufficient to reduce sugar intake by up to 100% by replacement with Acesulfame K.

78. A method of reducing bitter taste attributed to a bitter tastant in an edible composition comprising:
    (a) adding an effective amount of a compound according to Formula (I), Formula (II), Formula (III), or Formula (IV), as described herein, or combinations thereof, or any one of Compounds 1-8, as described herein, or combinations thereof, to the edible composition such that any bitter taste induced by the bitter tastant is reduced.

79. A method of reducing bitter taste attributed to a bitter tastant in an edible composition comprising:
    (a) ingesting an effective amount of a compound according to Formula (I), Formula (II), Formula (III), or Formula (IV), as described herein, or combinations thereof, or any one of Compounds 1-8, as described herein, or combinations thereof, along with the edible composition such that any bitter taste induced by the bitter tastant is reduced.

80. The method according to any one of paragraphs 35-79 or 81-90, wherein the edible composition is a food product, a consumer product, or a pharmaceutical composition.

81. The method according to any one of paragraphs 78-79, wherein the bitter taste induced by the bitter tastant is reduced by up to 25%

82. The method according to any one of paragraphs 78-79, wherein the bitter taste induced by the bitter tastant is reduced by up to 50%

83. The method according to any one of paragraphs 78-79, wherein the bitter taste induced by the bitter tastant is reduced by up to 75%

84. The method according to any one of paragraphs 78-79, wherein the bitter taste induced by the bitter tastant is reduced by up to 100%

85. The method according to any one of paragraphs 78, 79, and 81-84, wherein the bitter tastant is a bitter tasting salt.

86. The method according to paragraph 85, wherein the bitter tasting salt is a magnesium salt, a calcium salt, or a potassium salt.

87. The method according to paragraph 86, wherein the potassium salt is KC or potassium lactate.

88. The method according to any one of paragraphs 78, 79 and 81-87, wherein the edible composition further comprises NaCl, sodium lactate, or sugar.

89. A method of preserving an edible composition comprising:
(a) providing an edible composition; and
(b) combining with the edible composition of (a) potassium lactate and a compound according to Formula (I), Formula (II), Formula (III), or Formula (IV), as described herein, or combinations thereof, or any one of Compounds 1-8, as described herein, or combinations thereof.

90. A method of reducing the amount of sodium in an edible composition while preserving the edible composition, the method comprising:
(a) replacing an amount of sodium lactate used in preparing an edible composition with an amount of potassium lactate; and
(b) incorporating into the edible composition an effective amount of a compound according to Formula (I), Formula (II), Formula (III), or Formula (IV), as described herein, or combinations thereof, or any one of Compounds 1-8, as described herein, or combinations thereof.

91. A method of inhibiting, reducing, or eliminating a bitter taste in a subject comprising:
(a) placing a compound according to Formula (I), Formula (II), Formula (III), or Formula (IV), as described herein, or combinations thereof, or any one of Compounds 1-8, as described herein, or combinations thereof in the oral cavity of the subject.

92. The method according to paragraph 91, wherein the bitter taste is due to a bitter tasting salt.

93. The method according to paragraph 92, wherein the bitter taste is due to a magnesium salt, a calcium salt, or a potassium salt.

94. The method according to paragraph 93, wherein the bitter taste is due to KCl or potassium lactate.

95. A pharmaceutical composition comprising:
(a) a bitter tasting pharmaceutical active ingredient; and
(b) a compound according to Formula (I), Formula (II), Formula (III), or Formula (IV), as described herein, or combinations thereof, or any one of Compounds 1-8, as described herein, or combinations thereof.

96. A pharmaceutical composition comprising:
(a) a pharmaceutical active ingredient;
(b) a bitter tastant; and
(c) a compound according to Formula (I), Formula (II), Formula (III), or Formula (IV), as described herein, or combinations thereof, or any one of Compounds 1-8, as described herein, or combinations thereof.

97. A consumer product comprising:
(a) a bitter tasting ingredient; and
(b) a compound according to Formula (I), Formula (II), Formula (III), or Formula (IV), as described herein, or combinations thereof, or any one of Compounds 1-8, as described herein, or combinations thereof.

98. A consumer product for reducing bitter taste of a bitter tastant, wherein said consumer product comprises:
(a) a compound according to Formula (I), Formula (II), Formula (III), or Formula (IV), as described herein, or combinations thereof, or any one of Compounds 1-8, as described herein, or combinations thereof.

99. A method of inhibiting a bitter taste receptor comprising:
(a) contacting the bitter taste receptor with a compound according to Formula (I), Formula (II), Formula (III), or Formula (IV), as described herein, or combinations thereof, or any one of Compounds 1-8, as described herein, or combinations thereof.

100. The method according to paragraph 99, wherein the bitter taste receptor is in the oral cavity of a subject.

101. The method according to paragraph 99, wherein the bitter taste receptor is in the gastrointestinal tract of a subject.

102. The method according to paragraph 99, wherein the bitter taste receptor is present in an in vitro assay.

BRIEF DESCRIPTION OF THE FIGURES

FIG. 1 shows taste test results using samples various concentrations of KCL in solid turkey that were analyzed using a Latin Square 2AFC design.

DETAILED DESCRIPTION OF THE INVENTION

In order that the invention described herein may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "aliphatic" refers to straight chain or branched hydrocarbons that are completely saturated or that contain one or more units of unsaturation. For example, aliphatic groups include substituted or unsubstituted linear or branched alkyl, alkenyl and alkynyl groups. Unless indicated otherwise, the term "aliphatic" encompasses both substituted and unsubstituted hydrocarbons.

The term "alkoxy" refers to O-alkyl substituent, wherein the alkyl portion may be optionally substituted. Examples of alkoxy substituents include, but are not limited to, methoxy, ethoxy, n-propoxy, isopropoxy and n-butoxy. Also explicitly included within the scope of the term "alkoxy" are O-alkenyl or O-alkynyl groups. In all cases, the alkyl, alkene and alkyne portions may be optionally substituted.

The term "alkyl" refers to both straight and branched saturated chains containing, for example, 1-3, 1-6, 1-9, or 1-12 carbon atoms. An alkyl group may be optionally substituted.

The term "alkylthio" refers to an S-alkyl substituent, wherein the alkyl portion may be optionally substituted. Examples of alkylthio substituents include, but are not limited to, methylthio, ethylthio and isopropylthio. Also explicitly included within the scope of the term "alkylthio" are S-alkenyl or S-alkynyl groups. In all cases, the alkyl, alkene and alkyne portions may be optionally substituted.

The term "alkenyl" refers to both straight and branched saturated chains containing, for example, 2-3, 2-6, 2-9, or 2-12 carbon atoms, and at least one carbon-carbon double bond. An alkenyl group may be optionally substituted.

The term "alkynyl" refers to both straight and branched saturated chains containing, for example, 2-3, 2-6, 2-9, or 2-12 carbon atoms, and at least one carbon-carbon triple bond. An alkynyl group may be optionally substituted.

The terms "artificial sweetener" and "sugar substitute" refer to a food additive that confers a sweet taste but has less caloric energy than sugar. In some instances, the caloric energy of the "artificial sweetener" or "sugar substitute" is negligible.

The term "bitter" or "bitter taste" as used herein refers to the perception or gustatory sensation resulting following the detection of a bitter tastant. The following attributes may contribute to bitter taste: astringent, bitter-astringent, metallic, bitter-metallic, as well as off-tastes, aftertastes and undesirable tastes including but not limited to freezer-burn and card-board taste, and/or any combinations of these. It is noted that, in the art, the term "off-taste" is often synonymous with "bitter taste." Without being limited by theory, the diversity of bitter tastes may reflect the large number of bitter receptors and the differential detection of bitter tastants by these receptors. Bitter taste as used herein includes activation of a bitter taste receptor by a bitter tastant. Bitter taste as used herein also includes activation of a bitter taste receptor by a bitter tastant followed by downstream signaling. Bitter taste as used herein also includes activation of a signaling pathway after stimulation by a bitter tastant. Bitter taste as used herein further includes perception resulting from signaling following the detection of a bitter tastant by a bitter taste receptor. Bitter taste as used herein further includes perception resulting from signaling following contacting a bitter taste receptor with a bitter tastant. Bitter taste can be perceived in the brain.

The term "bitter taste receptor" refers to a receptor, typically a cell surface receptor, to which a bitter tastant can bind. Bitter taste receptors may be present in the oral cavity, and/or extra-oral tissues, e.g., in taste-like, hormone producing cells throughout the gastrointestinal tract, including the stomach, intestines, and colon. Bitter receptors can also be present in vitro, such as in an assay, including but not limited to a cell based assay or a binding assay.

The term "bitter tastant," "bitter ligand," or "bitter compound" refers to a compound that activates or that can be detected by a bitter taste receptor and/or confers the perception of a bitter taste in a subject. A "bitter tastant" also refers to a multiplicity of compounds that combine to activate or be detected by a bitter taste receptor and/or confer the perception of a bitter taste in a subject. A "bitter tastant" further refers to a compound that is enzymatically modified upon ingestion by a subject to activate or be detected by a bitter taste receptor and/or confer the perception of a bitter taste in a subject. Because the perception of bitter taste may vary from individual to individual, some individuals may describe a "bitter tastant" as a compound which confers a different kind of bitter taste compared to the kind of bitter taste perceived for the same compound by other individuals. The term bitter tastant also refers to a compound which confers a bitter taste. Those of skill in the art can readily identify and understand what is meant by a bitter tastant. Non-limiting examples of bitter tastants or substances including foods that comprise a bitter tastant and taste bitter include coffee, unsweetened cocoa, marmalade, bitter melon, beer, bitters, citrus peel, dandelion greens, escarole, quinine, magnesium salts, calcium salts, potassium salts, KCl, potassium lactate, Acesulfame K, Brussels sprouts, asparagus, bitter gourd, wild cucumber, celery, hops, kohlrabi, radish leaf, ginseng, pumpkin, collard greens, kale, sparteine, caffeine, atropine, nicotine, urea and strychnine.

Further examples of bitter tastants include pharmaceuticals. Non-limiting examples of pharmaceuticals as bitter tastants include acetaminophen, ampicillin, azithromycin, chlorpheniramine, cimetidine, dextromethorphan, diphenhydramine, erythromycin, ibuprofen, penicillin, phenylbutazone, psuedoephedrine, ranitidine, spironolactone and theophylline all of which have been associated with bitter taste.

The term "comestibly or biologically acceptable salt" refers to any comestibly or biologically acceptable salt, ester, or salt of such ester, of a compound of the present invention, which, upon ingestion, is capable of providing (directly or indirectly) a compound of the present invention, or a metabolite, residue or portion thereof, characterized by the ability to reduce the perception of a bitter taste attributed to a bitter tastant. Similarly, the term "comestibly or biologically acceptable derivative" refers to any comestibly or biologically acceptable derivative of a compound of the present invention, which, upon ingestion, is capable of providing (directly or indirectly) a compound of the present invention, or a metabolite, residue or portion thereof, characterized by the ability to reduce the perception of a bitter taste attributed to a bitter tastant. A "comestible product" is a product suitable for oral use, such as eating or drinking. Therefore, a comestibly acceptable compound is an edible compound.

The term "consumer product" refers to health and beauty products for the personal use and/or consumption by a subject. Consumer products may be present in any form including, but not limited to, liquids, solids, semi-solids, tablets, capsules, lozenges, strips, powders, gels, gums, pastes, slurries, syrups, aerosols and sprays. Non-limiting examples of consumer products include nutriceuticals, nutritional supplements, lipsticks, lip balms, soaps, shampoos, gums, adhesives (e.g., dental adhesives), toothpastes, oral analgesics, breath fresheners, mouthwashes, tooth whiteners, and other dentifrices.

The term "diet" collectively refers to the food products and/or beverages consumed by a subject. A subject's "diet" also includes any consumer products or pharmaceutical compositions the subject ingests.

The term "edible composition" refers to a composition suitable for consumption, typically via the oral cavity (although consumption may occur via non-oral means such as inhalation). Edible compositions may be present in any form including, but not limited to, liquids, solids, semi-solids, tablets, lozenges, powders, gels, gums, pastes, slurries, syrups, aerosols and sprays. As used herein, edible compositions include food products, pharmaceutical compositions, and consumer products. The term edible compositions also refers to, for example, dietary and nutritional supplements. As used herein, edible compositions also include compositions that are placed within the oral cavity but not swallowed, including professional dental products, such as dental treatments, fillings, packing materials, molds and polishes. The term "comestible" refers to similar compositions and is generally used as a synonym to the term "edible."

The term "effective amount" refers to an amount sufficient to produce a desired property or result. For example, an effective amount of a compound of the present invention is an amount capable of reducing the perception of bitter taste associated with a bitter tastant. The term "effective amount" of a compound of the invention also refers to an amount which, when added to an edible composition, reduces the bitter taste of, e.g., a NaCl substitute, thereby allowing for the maintenance of the perception of a desired salty flavor of a said edible composition. The term "effective amount of a compound" also refers to an amount which, when added to an edible composition, allows for the preservation of a food product, while reducing or eliminating bitter taste associated with a bitter tastant in the preservative. The term "effective amount" also refers to the amount of a compound of the present invention capable or reducing or eliminating the perception of a bitter taste or aftertaste associated with either a bitter tastant in a food product or an inherently bitter food product.

The term "flavor modifier" refers to a compound or a mixture of compounds that, when added to an edible composition, such as a food product, modifies (e.g., masks, eliminates, decreases, reduces, or enhances the perception of) a flavor (e.g., sweet, salty, umami, sour, or bitter taste) present in the edible composition.

The term "food product" refers to any composition comprising one or more processed foodstuff. Food products include, but are not limited to, confectionaries, bakery products (including, but not limited to, doughs, breads, biscuits, crackers, cakes, pastries, pies, tarts, quiches, and cookies), ice creams (including but not limited to impulse ice cream, take-home ice cream, frozen yogurt, gelato, sorbet, sherbet and soy, oat, bean and rice-based ice cream), dairy products (including, but not limited to, drinking milk, cheese, yogurt, and sour milk drinks), cheeses (including, but not limited to, natural cheeses and processed cheeses), butter, margarine, sweet and savory snacks (including but not limited to fruit snacks, chips/crisps, tortilla/corn chips, popcorn, pretzels, chocolates, and nuts), hot and cold beverages (including, but not limited to, beverages, beverage mixes, concentrates, juices, carbonated beverages, non-carbonated beverages, alcoholic beverages, non-alcoholic beverages, soft drinks, sports drinks, isotonic drinks, coffees, teas, bottled waters, and beverages prepared from botanicals and botanical extracts (including cold beverages that are prepared with botanical or fungi extracts as ingredients, and drinks that are prepared in various ways, such as infusions, decoctions, or other means of extraction or distillation of various plant parts, including, but not limited to leaves, flowers, stems, fruits, roots, rhizomes, stems, bark, volatile oils, or even the whole plant)), snack bars (including, but not limited to granola bars, muesli bars, protein bars, breakfast bars, energy bars, and fruit bars), meal replacement products, ready meals (including, but not limited to canned meals, preserved meals, frozen meals, dried meals, chilled meals, dinner mixes, macaroni and cheese, frozen pizza, chilled pizza, and prepared salads), soups (including but not limited to broth-like soups and cream-based soups), broth, gravy, soy sauce, meats and fish (including raw, cooked, and dried meats), deli products (including but not limited to meats and cheeses suitable for slicing or pre-sliced meats and cheeses, e.g., turkey, chicken, ham, bologna, salami, bierwurst, capicola, chorizo, corned beef, dutch loaf, Serrano, prosciutto, head cheese, liverwurst, meatloaf (including olive loaf, pepper loaf, pimento loaf, and ham and cheese loaf), mortadella, pastrami, pepperoni, roast beef, roast pork, saucisson, smoked meat, summer sausage, tongue, American cheese, blue cheese, cheddar cheese, Colby cheese, Colby-Jack cheese, gouda, Monterey Jack cheese, muenster cheese mozzarella, parmigiano cheese, pepper jack cheese, provolone, romano cheese, string cheese, spray cheese, and swiss cheese), vegetables (including, but not limited to, raw, pickled, cooked, and dried vegetables, such as french fries), fruits (including raw, cooked, and dried fruits), grains (including, but not limited to, dried cereals and breads), prepared foods (including, but not limited to, dried, canned, or jarred sauces and soups), snack foods, pastas (including, but not limited to, fresh pasta, chilled pasta, frozen pasta, dried pasta, and macaroni), noodles (including, but not limited to, egg noodles, wheat noodles, rice noodles, mung bean noodles, potato noodles, buckwheat noodles, corn noodles, cellophane noodles, chow mein, fettuccini, fusilli, gnocchi, lasagna, linguini, lo mein, macaroni, manicotti, pad thai, penne, ramen, rice vermicelli, rigatoni, soba, spaghetti, spatzle, udon, and ziti), canned foods, frozen foods, dried foods, chilled foods, oils and fats, baby food, spreads, salads, cereals (including, but not limited to, hot and cold cereals), sauces (including, but not limited to, cheese sauces (e.g., for macaroni and cheese) tomato pastes, tomato purees, bouillon cubes, stock cubes, table sauces, boys bases sauces, pasta sauces, cooking sauces, marinades, dry sauces, powder mixes, ketchups, mayonnaises, salad dressings, vinegrettes, mustards, and dips), jellies, jams, preserves, honey, puddings, recipe mixes, syrups, icings, fillings, infused foods, salt-preserved food, marinated foods and condiments (such as ketchup, mustard and steak sauce). In some embodiments, the food product is animal feed. For example, the food product may be a pet food product, i.e. a food product for consumption by a household pet. In other embodiments, the food product is a livestock food product, i.e. a food product for consumption by livestock.

The term "foodstuff" refers to an unprocessed ingredient or a basic nutrient or flavor containing element used to prepare a food product. Non-limiting examples of foodstuffs include: fruits, vegetables, meats, fishes, grains, milks, eggs, tubers, sugars, sweeteners, oils, herbs, snacks, sauces, spices and salts.

The term "halo" or "halogen" refers to a fluorine, chlorine, bromine or iodine substituent.

The terms "parts per million" and "ppm" are used in the food industry to refer to a low concentration of a solution. For example, one gram of solute in 1000 ml of solvent has a concentration of 1000 ppm and one thousandth of a gram (0.001 g) of solute in 1000 ml of solvent has a concentration of one ppm. Accordingly, a concentration of one milligram per liter (i.e. 1 mg/L) is equal to 1 ppm.

The terms "perception of a bitter taste," "perception of saltiness," "perception of a flavor" and similar terms, refer to the awareness of a subject of a particular taste or flavor.

The term "pharmaceutically active ingredient" refers to a compound in a pharmaceutical composition which is biologically active.

The term "potassium salt" refers to a salt wherein potassium is the cation. Potassium salts in the context of the present invention are preferably edible potassium salts including, but not limited to, Acesulfame K (Ace K), aluminum potassium sulfate, dipotassium guanylate, dipotassium inosinate, monopotassium glutamate, potassium acetate, potassium acid tartate, potassium acid tartrate, potassium adipate, potassium alginate, potassium aluminum silicate, potassium ascorbate, potassium aspartate, potassium benzoate, potassium bicarbonate, potassium bisulfate, potassium bisulfite, potassium bromate, potassium carbonate, potassium chloride, potassium citrate, potassium dihydrogen citrate, potassium dihydrogen phosphate, potassium ferrocyanide, potassium fumarate, potassium gibberellate, potassium gluconate, potassium hydroxide, potassium hydrogen sulfite, potassium iodide, potassium lactate, potassium malate, potassium metabisulfite, potassium nitrate, potassium nitrite, potassium persulfate, potassium phosphate (dibasic), potassium phosphate (monobasic), potassium phosphate (tribasic), potassium polymetaphosphate, potassium polyphosphates, potassium pyrophosphate, potassium propionate, potassium saccharin, potassium sodium tartrate (e.g., potassium sodium L(+)-tartrate), potassium sorbate, potassium sulfate, potassium sulfite, and potassium tripolyphosphate.

The term "processed foodstuff" refers to a foodstuff has been subjected to any process which alters its original state (excluding. e.g., harvesting, slaughtering, and cleaning). Examples of methods of processing foods include, but are not limited to, removal of unwanted outer layers, such as potato peeling or the skinning of peaches; chopping or slicing; mincing or macerating; liquefaction, such as to produce fruit juice; fermentation (e.g. beer); emulsification; cooking, such as boiling, broiling, frying, heating, steaming or grilling; deep frying; baking; mixing; addition of gas such as air entrainment for bread or gasification of soft drinks; proofing; seasoning (with, e.g., herbs, spices, salts); spray drying; pasteurization; packaging (e.g., canning or boxing); extrusion; puffing; blending; and preservation (e.g., adding salt, sugar, potassium lactate or other preservatives).

The term "replace" or "replacing" refers to substituting one compound for another compound in or in the preparation of, for example, an edible composition, such as food product. It includes complete and partial replacements or substitutions.

The term "salty flavor" refers to the taste elicited by, for example, ions of alkali metals salts (e.g., Na$^+$ and Cl$^-$ in sodium chloride). Non-limiting examples of compositions eliciting a salty flavor include table salt (sodium chloride), sea water, sea salt and potassium chloride. The amount of salty flavor or the saltiness of a composition can be determined by, e.g., taste testing.

The term "sodium" or "sodium salt" refers to the amount of sodium (i.e., sodium salt) ingested or otherwise consumed by a subject. In general, "sodium" or a "sodium salt" refers to a salt or compound wherein sodium is the cation. Sodium salts in the context of the present invention include, but are not limited to, aluminum sodium sulfate, calcium disodium EDTA, dioctyl sodium sulfosuccinate, disodium 5'-ribonucleotides, disodium ethylenediaminetetraacetate, disodium guanylate, disodium inosinate sodium acetate, monosodium glutamate (MSG), potassium sodium tartrate, sodium acid pyrophosphate, sodium adipate, sodium alginate, sodium aluminosilicate, sodium aluminum phosphate (acidic), sodium aluminum phosphate (basic), sodium ascorbate, sodium benzoate, sodium bicarbonate, sodium bisulfate, sodium bisulfite, sodium carbonate, sodium carboxymethylcellulose, sodium caseinate, sodium chloride, sodium citrate, sodium cyclamate, sodium dehydroacetate, sodium diacetate, sodium dehydroacetate, sodium dihydrogen citrate, sodium dihydrogen phosphate, sodium DL-malate, sodium erythorbate, sodium erythorbin, odium ethyl para-hydroxybenzoate, sodium ferric pyrophosphate, sodium ferrocyanide, sodium formate, sodium fumarate, sodium gluconate, sodium hydrogen carbonate, sodium hydrogen DL-malate, sodium hydrogen acetate, sodium hydrogen sulfite, sodium hydroxide, sodium hypophosphite, sodium tartrate (e.g., sodium L(+)-tartrate), sodium lactate, sodium lauryl sulfate, sodium malate, sodium metabisulfite, sodium metaphosphate, sodium methyl para-hydroxybenzoate, sodium nitrate, sodium nitrite, sodium O-phenylphenol, sodium phosphate (dibasic), sodium phosphate (monobasic), sodium phosphate (tribasic), sodium polyphosphate, sodium potassium tartrate, sodium propionate, sodium propyl para-hydroxybenzoate, sodium pyrophosphate, sodium saccharin, sodium sesquicarbonate, sodium stearoyl lactylate, sodium stearyl fumarate, sodium succinate, sodium sulfate, and starch sodium octenylsuccinate.

The term "sodium intake" refers to the amount of sodium ingested or otherwise consumed by a subject.

The term "stability" or "stable" in the context of a chemical structure refers to the chemical state when a system is in its lowest energy state, or in chemical equilibrium with its environment. Thus, a stable compound (or, e.g., a compound containing a number of atoms or substitutions that are stable) is not particularly reactive in the environment or during normal use, and retains its useful properties on the timescale of its expected usefulness.

The term "subject" refers to a mammal. In preferred embodiments, the subject is human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include: alpaca, bison, camel, cattle, deer, pigs, horses, llamas, mules, donkeys, sheep, goats, rabbits, reindeer, and yak.

The term "sugar" refers to a simple carbohydrate, such as a monosaccharide or a disaccharide, that delivers a primary taste sensation of sweetness. Non-limiting examples of sugar include glucose, fructose, galactose, sucrose, lactose, and maltose.

The term "sweet flavor" refers to the taste elicited by, for example, sugars. Non-limiting examples of compositions eliciting a sweet flavor include glucose, sucrose, fructose, saccharin, cyclamate, aspartame, acesulfame potassium, sucralose, alitame, and neotame. The amount of sweet flavor or the sweetness of a composition can be determined by, e.g., taste testing.

An aliphatic group may contain one or more substituents. Examples of suitable substituents on a saturated or unsaturated carbon of an aliphatic group include, but are not limited to, halogen, —CF$_3$, —R', —OR', —OH, —SH, —SR', protected OH (such as acyloxy), —NO$_2$, —CN, —NH$_2$, —NHR', —N(R')$_2$, —NHCOR', —NHCONH$_2$, —NHCONHR', —NHCON(R')$_2$, —NRCOR', —NHCO$_2$H, —NHCO$_2$R', —CO$_2$R', —CO$_2$H, —COR', —CONH$_2$, —CONHR', —CON(R')$_2$, —S(O)$_2$H, —S(O)$_2$R', —S(O)$_3$H, —S(O)$_3$R', —S(O)$_2$NH2'-S(O)H, —S(O)R', —S(O)$_2$NHR', —S(O)$_2$N(R')$_2$, —NHS(O)$_2$H, or —NHS(O)$_2$R', =O, =S, =NNHR', =NN(R')$_2$, =N—OR', =NNHCOR', =NNHCO$_2$R', =NNHSO$_2$R', =N—CN, or =NR', wherein R' is selected from H, aliphatic, carbocyclyl, heterocyclyl, aryl, aralkyl, heteroaryl, or heteroaralkyl and each R' is optionally substituted with one or more halogen, nitro, cyano, amino, —NH-(unsubstituted aliphatic), —N-(unsubstituted aliphatic)$_2$, carboxy, carbamoyl, hydroxy, —O-(unsubstituted aliphatic), —SH, —S-(unsubstituted aliphatic), CF$_3$, —S(O)$_2$NH$_2$' unsubstituted aliphatic, unsubstituted carbocyclyl, unsubstituted heterocyclyl, unsubstituted aryl, unsubstituted aralkyl, unsubstituted heteroaryl, or unsubstituted heteroaralkyl. Guided by this specification, the selection of suitable substituents is within the knowledge of one skilled in the art.

As defined herein, the compounds of the invention are intended to include all stereochemical forms of the compound, including geometric isomers (i.e., E, Z) and optical isomers (i.e., R, S). Single stereochemical isomers as well as enantiomeric and diastereomeric mixtures of the present compounds are within the scope of the invention. Unless otherwise stated, formulas depicted herein are also meant to include compounds which differ only in the presence of one or more isotopically enriched atoms. For example, compounds having the present formulas except for the replacement of a hydrogen by a deuterium or tritium, or the replacement of a carbon by a $^{13}C$- or $^{14}C$-enriched carbon are within the scope of this invention.

The present invention provides edible compositions comprising a compound of the present invention, including food products, consumer products, and pharmaceutical compositions comprising said compounds, and methods of preparing a such compositions. The present invention also provides methods of reducing the amount of sodium (e.g., NaCl or sodium lactate) or sugar in a food product, a method of reducing the sodium or sugar intake in a diet, a method of reducing bitter taste, and a method of reducing the activity of a bitter taste receptor. The present invention also includes reducing the amount of sodium in a edible composition or diet by replacing a sodium containing compound or composition with a potassium containing compound or composition. The present invention also includes reducing the amount of sugar in a edible composition or diet by replacing sugar with a potassium containing sweetener, such as Acesulfame K.

Edible Compositions

According to one aspect, the invention provides an edible composition comprising a compound of the invention for reducing bitter taste of a bitter tastant.

All stereochemical forms of the compounds disclosed in this and any section herein are specifically contemplated, including geometric isomers (i.e., E, Z) and optical isomers (i.e., R, S). Single stereochemical isomers as well as enantiomeric and diastereomeric mixtures of the compounds disclosed in this and any section herein are also specifically contemplated.

In some embodiments, the present invention provides an edible composition for reducing bitter taste of a bitter tastant, wherein the composition comprises a branched alkene compound. The branched alkene compounds of this invention are capable of reducing or eliminating bitter taste of a bitter tastant. In some embodiments, the branched alkene compound has a molecular weight less than about 1000, 500, or 300 daltons. In certain embodiments, the branched alkene compound is a compound of Formula (I):

Formula (I)

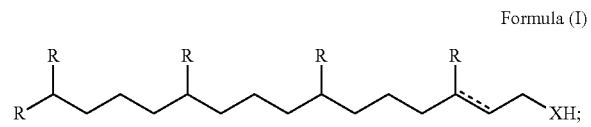

or a comestibly or biologically acceptable salt or derivative thereof, or an enantiomer or diastereomer thereof, wherein, as valence and stability permit:

X is S or O;
each R is independently H, $C_1$-$C_6$ alkyl, $C_2$-$C_6$ alkenyl, or $C_2$-$C_6$ alkynyl; and
the dotted bond represents an optional carbon-carbon double bonds;

wherein the composition is edible and capable of reducing bitter taste of a bitter tastant.

According to some embodiments of compounds of Formula (I),
as valence and stability permit:
X is S or O;
each R is independently H, $C_1$-$C_3$ alkyl, $C_2$-$C_3$ alkenyl, or $C_2$-$C_3$ alkynyl; and
the dotted bond represents an optional carbon-carbon double bond.

According to some embodiments of compounds of Formula (I),
as valence and stability permit:
X is O;
each R is independently H, $C_1$-$C_3$ alkyl, $C_2$-$C_3$ alkenyl, or $C_2$-$C_3$ alkynyl; and
the dotted bond represents an optional carbon-carbon double bond.

According to some embodiments of compounds of Formula (I),
as valence and stability permit:
X is S or O;
each R is independently H or $C_1$-$C_3$ alkyl; and
the dotted bond represents an optional carbon-carbon double bond.

According to some embodiments of compounds of Formula (I),
as valence and stability permit:
X is O;
each R is independently H or $C_1$-$C_3$ alkyl; and
the dotted bond represents an optional carbon-carbon double bond.

In certain embodiments, the compound of Formula (I) includes an E-double bond where the dotted bond is located. In other embodiments, the compound of Formula (I) includes a Z-double where the dotted bond is located. In further embodiments, the compound of Formula (I) includes a mixture of E/Z-double bonds where the dotted bond is located. In yet additional embodiments, the compound of Formula (I) does not include a double bond where the dotted bond is located.

In certain embodiments, the compound of Formula (I) is:

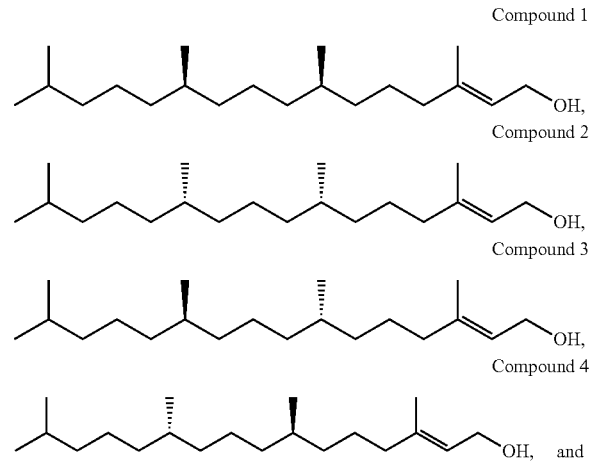

Compound 5

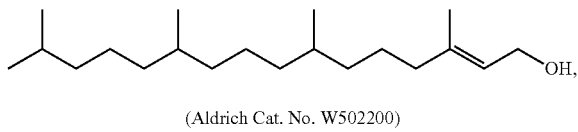

(Aldrich Cat. No. W502200)

or a comestibly or biologically acceptable salt or derivative thereof, or an enantiomer or diastereomer thereof.

If a comestibly or biologically acceptable salt of a compound of the present invention is used, such salt is preferably derived from inorganic or organic acids and bases. Examples of such salts include, but are not limited to, those derived from appropriate bases, including alkali metal (e.g., sodium and potassium), alkaline earth metal (e.g., magnesium), ammonium and $N^+(C_{1-4}$ alkyl$)_4$ salts.

In some embodiments, the present invention provides an edible composition for reducing bitter taste of a bitter tastant, wherein the composition comprises a cyclohexadiene-based compound. The cyclohexadiene-based compounds of this invention are capable of reducing or eliminating bitter taste of a bitter tastant. In some embodiments, the cyclohexadiene-based compound has a molecular weight less than about 1000, 500, 300 or 200 daltons. In certain embodiments, the cyclohexadiene-based compound is a compound of Formula (II):

Formula (II)

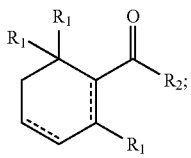

or a comestibly or biologically acceptable salt or derivative thereof, or an enantiomer or diastereomer thereof,
wherein, as valence and stability permit:
each $R_1$ is independently H, $C_1$-$C_6$ alkyl, $C_2$-$C_6$ alkenyl, or $C_2$-$C_6$ alkynyl;
$R_2$ is H, $C_1$-$C_6$ alkyl, $C_2$-$C_6$ alkenyl, or $C_2$-$C_6$ alkynyl; and
the dotted bonds represent optional carbon-carbon double bonds;
wherein the composition is edible and capable of reducing bitter taste of a bitter tastant.

According to some embodiments of compounds of Formula (II).
as valence and stability permit:
each $R_1$ is independently H, $C_1$-$C_3$ alkyl, $C_2$-$C_3$ alkenyl, or $C_2$-$C_3$ alkynyl;
$R_2$ is H, $C_1$-$C_3$ alkyl, $C_2$-$C_3$ alkenyl, or $C_2$-$C_3$ alkynyl; and
the dotted bonds represent optional carbon-carbon double bonds.

According to some embodiments of compounds of Formula (II),
as valence and stability permit:
each $R_1$ is independently H or $C_1$-$C_3$ alkyl;
$R_2$ is H, $C_1$-$C_3$ alkyl or $C_2$-$C_3$ alkenyl; and
the dotted bonds represent optional carbon-carbon double bonds.

According to some embodiments of compounds of Formula (II).
as valence and stability permit:
each $R_1$ is independently H or $C_1$-$C_3$ alkyl;
$R_2$ is H or $C_2$-$C_3$ alkenyl; and
the dotted bonds represent optional carbon-carbon double bonds.

According to some embodiments of compounds of Formula (II),
as valence and stability permit:
each $R_1$ is independently H or $C_1$-$C_3$ alkyl;
$R_2$ is H or $C_2$-$C_3$ alkenyl; and
each dotted line is a carbon-carbon double bond.

In certain embodiments of the compound of Formula (II), the exocyclic double bond is an E-double bond. In other embodiments of the compound of Formula (II), the exocyclic double bond is a Z-double bond. In further embodiments, the compound of Formula (II) includes a mixture of E/Z-exocyclic double bonds. In yet additional embodiments, the compound of Formula (II) does not include an exocyclic double bond.

In certain embodiments, the compound of Formula (II) is:

Compound 6

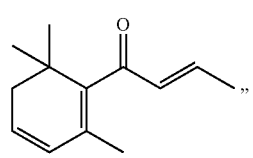

(Sigma Cat. W342017)

or a comestibly or biologically acceptable salt or derivative thereof, or an enantiomer or diastereomer thereof.

In some embodiments, the present invention provides an edible composition for reducing bitter taste of a bitter tastant, wherein the composition comprises a branched alkene ester compound. The branched alkene ester compounds of this invention are capable of reducing or eliminating bitter taste of a bitter tastant. In some embodiments, the branched alkene ester compound has a molecular weight less than about 1000, 500 or 300 daltons. In certain embodiments, the alkene ester compound is a compound of Formula (III):

Formula (III)

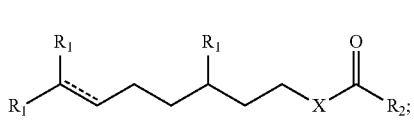

or a comestibly or biologically acceptable salt or derivative thereof, or an enantiomer or diastereomer thereof,
wherein, as valence and stability permit:
X=S or O;
each $R_1$ is independently H, $C_1$-$C_6$ alkyl, $C_2$-$C_6$ alkenyl, or $C_2$-$C_6$ alkynyl;
$R_2$ is H, $C_1$-$C_{10}$ alkyl, $C_2$-$C_{10}$ alkenyl, or $C_2$-$C_{10}$ alkynyl; and
the dotted bond represents an optional carbon-carbon double bond;
wherein the composition is edible and capable of reducing bitter taste of a bitter tastant.

According to some embodiments of compounds of Formula (III),
as valence and stability permit:
X=S or O;
each $R_1$ is independently H, $C_1$-$C_6$ alkyl, $C_2$-$C_6$ alkenyl, or $C_2$-$C_6$ alkynyl;

$R_2$ is H, $C_3$-$C_6$ alkyl, $C_2$-$C_6$ alkenyl, or $C_2$-$C_6$ alkynyl; and the dotted line represents an optional carbon-carbon double bond.

According to some embodiments of compounds of Formula (III),
as valence and stability permit:
X=S or O;
each $R_1$ is independently H, $C_1$-$C_3$ alkyl, $C_2$-$C_3$ alkenyl, or $C_2$-$C_3$ alkynyl;
$R_2$ is H, $C_1$-$C_6$ alkyl, $C_2$-$C_6$ alkenyl, or $C_2$-$C_6$ alkynyl; and the dotted line represents an optional carbon-carbon double bond.

According to some embodiments of compounds of Formula (III),
as valence and stability permit:
X=O;
each $R_1$ is independently H, $C_1$-$C_3$ alkyl, $C_2$-$C_3$ alkenyl, or $C_2$-$C_3$ alkynyl;
$R_2$ is H, $C_1$-$C_6$ alkyl, $C_2$-$C_6$ alkenyl, or $C_2$-$C_3$ alkynyl; and the dotted line represents an optional carbon-carbon double bond.

According to some embodiments of compounds of Formula (III),
as valence and stability permit:
X=S or O;
each $R_1$ is independently H, $C_1$-$C_3$ alkyl, $C_2$-$C_3$ alkenyl, or $C_2$-$C_3$ alkynyl;
$R_2$ is H, $C_1$-$C_4$ alkyl, $C_2$-$C_4$ alkenyl, or $C_2$-$C_4$ alkynyl; and the dotted line represents an optional carbon-carbon double bond.

According to some embodiments of compounds of Formula (III),
as valence and stability permit:
X=O;
each $R_1$ is independently H, $C_1$-$C_3$ alkyl, $C_2$-$C_3$ alkenyl, or $C_2$-$C_3$ alkynyl;
$R_2$ is H, $C_1$-$C_4$ alkyl, $C_2$-$C_4$ alkenyl, or $C_2$-$C_4$ alkynyl; and the dotted line represents an optional carbon-carbon double bond.

According to some embodiments of compounds of Formula (III),
as valence and stability permit:
X=O;
each $R_1$ is independently H, $C_1$-$C_3$ alkyl, $C_2$-$C_3$ alkenyl, or $C_2$-$C_3$ alkynyl;
$R_2$ is H, $C_1$-$C_4$ alkyl, $C_2$-$C_4$ alkenyl, or $C_2$-$C_4$ alkynyl; and the dotted line is a carbon-carbon double bond.

In certain embodiments, the compound of Formula (III) includes an E-double bond where the dotted bond is located. In other embodiments, the compound of Formula (III) includes a Z-double where the dotted bond is located. In further embodiments, the compound of Formula (III) includes a mixture of E/Z-double bonds where the dotted bond is located. In yet additional embodiments, the compound of Formula (III) does not include a double bond where the dotted bond is located.

In certain embodiments, the compound of Formula (III) is:

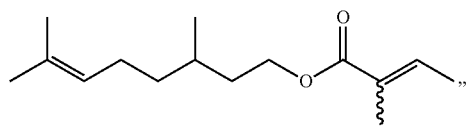

Compound 7

(Sigma Cat. No. W500607)

or a comestibly or biologically acceptable salt or derivative thereof, or an enantiomer or diastereomer thereof.

If a comestibly or biologically acceptable salt of a compound of the present invention is used, such salt is preferably derived from inorganic or organic acids and bases. Examples of such salts include, but are not limited to, those derived from appropriate bases, including alkali metal (e.g., sodium and potassium), alkaline earth metal (e.g., magnesium), ammonium and $N^+(C_{1-4}$ alkyl$)_4$ salts.

In some embodiments, the present invention provides an edible composition for reducing bitter taste of a bitter tastant, wherein the composition comprises a benzodioxole-based compound. The benzodioxole-based compounds of this invention are capable of reducing or eliminating bitter taste of a bitter tastant. In some embodiments, the benzodioxole-based compound has a molecular weight less than about 1000, 500, 300 or 200 daltons. In certain embodiments, the benzodioxole-based compound is a compound of Formula (IV):

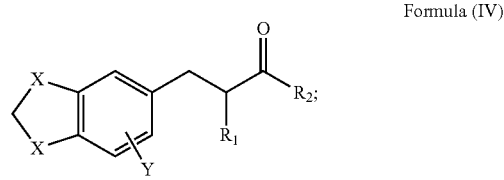

Formula (IV)

or a comestibly or biologically acceptable salt or derivative thereof, or an enantiomer or diastereomer thereof,
wherein, as valence and stability permit:
each X is independently S or O;
Y=H or halogen;
$R_1$ is H, $C_1$-$C_6$ alkyl, $C_2$-$C_6$ alkenyl, or $C_2$-$C_6$ alkynyl; and
$R_2$ is H, $C_1$-$C_6$ alkyl, $C_2$-$C_6$ alkenyl, or $C_2$-$C_6$ alkynyl;
wherein the composition is edible and capable of reducing bitter taste of a bitter tastant.

According to some embodiments of compounds of Formula (IV),
as valence and stability permit:
each X is independently S or O;
Y=H or halogen;
$R_1$ is H, $C_1$-$C_3$ alkyl, $C_2$-$C_3$ alkenyl, or $C_2$-$C_3$ alkynyl; and
$R_2$ is H, $C_2$-$C_3$ alkyl, $C_2$-$C_3$ alkenyl, or $C_2$-$C_3$ alkynyl.

According to some embodiments of compounds of Formula (IV),
as valence and stability permit:
each X is independently S or O;
Y=H or halogen;
$R_1$ is H, $C_1$-$C_3$ alkyl, $C_2$-$C_3$ alkenyl, or $C_2$-$C_3$ alkynyl; and
$R_2$ is H or $C_1$-$C_3$ alkyl.

According to some embodiments of compounds of Formula (IV),
as valence and stability permit:
X=O;
Y=H;
$R_1$ is H, $C_1$-$C_3$ alkyl, $C_2$-$C_3$ alkenyl, or $C_2$-$C_3$ alkynyl; and
$R_2$ is H or $C_1$-$C_3$ alkyl.

According to some embodiments of compounds of Formula (IV),
as valence and stability permit:
X=O;
Y=H;
$R_1$ is H or $C_1$-$C_3$ alkyl; and
$R_2$ is H or $C_1$-$C_3$ alkyl.

According to some embodiments of compounds of Formula (IV),
as valence and stability permit:
X=O;
Y=H;
R₁ is H or C₁-C₃ alkyl; and
R₂ is H.
In certain embodiments, the compound of Formula (IV) is:

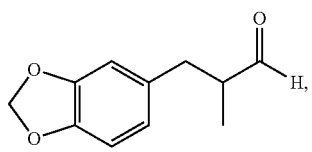

Compound 8

(Sigma Cat. No. W523909)

or a comestibly or biologically acceptable salt or derivative thereof, or an enantiomer or diastereomer thereof.

If a comestibly or biologically acceptable salt of a compound of the present invention is used, such salt is preferably derived from inorganic or organic acids and bases. Examples of such salts include, but are not limited to, those derived from appropriate bases, including alkali metal (e.g., sodium and potassium), alkaline earth metal (e.g., magnesium), ammonium and N⁺(C₁₋₄ alkyl)₄ salts.

Another aspect of the present invention provides edible compositions comprising a) a compound of the invention; and b) a bitter tastant. In some embodiments, the compound is a compound having a molecular weight less than about 1000, 500, or 300 daltons. In certain embodiments, the compound is a compound of Formula (I), Formula (II), Formula (III), or Formula (IV), as described herein, or combinations thereof. In some embodiments, the compound of the invention is a compound selected from Compounds 1-8, as described herein, or combinations thereof.

In some embodiments, the bitter tastant present in the edible composition is a bitter tasting salt. In some embodiments, the bitter tastant present in the edible composition is a potassium salt, a magnesium salt, or a calcium salt. In some embodiments, the bitter tastant present in the edible composition is a potassium salt. In some embodiments, the bitter tastant present in the edible compositions is KCl. In other embodiments, the bitter tastant present in the edible composition is potassium lactate.

In another embodiment, the edible compositions comprise a) a compound of the invention; and b) a potassium salt. In some embodiments, the potassium salt is KCl or potassium lactate. In specific embodiments, the potassium salt is KCl. In certain embodiments, the compound is a compound of Formula (I), Formula (II), Formula (III), or Formula (IV), as described herein, or combinations thereof. In some embodiments, the compound of the invention is a compound selected from Compounds 1-8, as described herein, or combinations thereof.

In some embodiments, the edible composition further comprises a sodium salt. In some embodiments, the edible compositions further comprise NaCl. In some embodiments, the edible compositions further comprise sodium lactate. In some embodiments, the edible compositions further comprise sugar.

In some embodiments, the edible composition further comprises one or more additional components selected from the group consisting of preservatives, nutritives, flavorants or additional flavor modifiers, which may lack an inherent flavor.

In some embodiments, the edible composition further comprises one or more emulsifiers. Sodium and potassium based emulsifiers are commonly used as emulsifiers in the food art. Sodium-based emulsifiers include, e.g., sodium salts of fatty acids, sodium alginate, sodium aluminum phosphate, sodium caseinate, sodium metaphosphate, sodium phosphate (dibasic), sodium phosphate (monobasic), sodium phosphate (tribasic), sodium polyphosphate, sodium pyrophosphate, and sodium stearoyl lactylate. Potassium-based emulsifiers include, e.g., potassium salts of fatty acids, potassium alginate, potassium citrate, potassium phosphate (dibasic), potassium phosphate (monobasic), potassium phosphate (tribasic), potassium polyphosphate, potassium polymetaphosphate, and potassium pyrophosphate. Accordingly, some embodiments of the present invention include replacing a sodium-based emulsifier with a potassium based emulsifier and adding a compound of the present invention.

In some embodiments, the edible composition further comprises a surfactant to increase or decrease the effectiveness of the compounds of the present invention. Suitable surfactants include, but are not limited to, non-ionic surfactants (e.g., mono and diglycerides, fatty acid esters, sorbitan esters, propylene glycol esters, and lactylate esters) anionic surfactants (e.g., sulfosuccinates and lecithin) and cationic surfactants (e.g., quaternary ammonium salts).

In some embodiments wherein the edible compositions further comprises a preservative, the preservative improves the shelf life of the edible composition. Suitable preservatives include, but are not limited to, ascorbic acid, benzoic acid, butyl p-hydroxybenzoate, calcium benzoate, calcium disodium EDTA, calcium hydrogen sulfite, calcium propionate, calcium sorbate, chitosan, cupric sulfate, dehydroacetic acid, diethyl pyrocarbonate, dimethyl dicarbonate, disodium EDTA, E-polylysine glycine, erythorbic acid, ethyl p-hydroxybenzoate, formic acid, gum guaiac, heptylparaben, hinokitiol, isobutyl paraoxybenzoate, Japanese styrax benzoin extract, methylparaben, milt protein extract, natamycin, nisin, peptin extract, 2-phenylphenol, pimaricin, potassium acetate, potassium benzoate, potassium lactate, potassium metabisulfite, potassium nitrate, potassium nitrite, potassium pyrosulfite, potassium sorbate, potassium sulfite, propionic acid, propyl p-hydroxybenzoate, propyl p-oxybenzoate, propylene oxide, propylparaben, sodium benzoate, sodium bisulfite, sodium dehydroacetate, sodium diacetate, sodium erythorbate, sodium hydrogen sulfite, sodium hypophosphite, sodium hyposulfite, sodium metabisulfite, sodium nitrate, sodium nitrite, sodium o-phenylphenol, sodium propionate, sodium pyrosulfite, sodium sulfite, sodium thiocyanate, sorbic acid and sulfur dioxide. In some embodiments, the preservative has a bitter flavor.

In some embodiments, the composition may further comprise one or more additional components selected from the group consisting of flow agents, processing agents, sugars, amino acids, other nucleotides, and sodium or potassium salts of organic acids such as citrate and tartarate. Such additional ingredients may add flavor, or aid in blending, processing or flow properties of the edible composition.

In some embodiments, the rate of release of the compound of the present invention is regulated. The release rate of the compound of the present invention can be altered by, for example, varying its solubility in water. Rapid release can be achieved by encapsulating the compound of the present invention with a material with high water solubility. Delayed release of the compound of the present invention can be achieved by encapsulating the compound of the present invention with a material with low water solubility. The compound of the present invention can be co-encapsulated with carbohydrates or masking tastants such as sweeteners. The rate of release of the compound of the present invention can also be regulated by the degree of encapsulation. In some embodiments, the compound of the present invention is fully encapsulated. In other embodiments, the compounds of the present invention are partially encapsulated. In some embodiments, the rate of release is regulated so as to release with the bitter tastant.

The edible compositions of this invention are prepared according to techniques well-known in the art. In general, an edible composition of the invention is prepared by mixing a component or ingredient of the edible composition with a compound of the invention. Alternatively, a compound of the invention can be added directly to the edible composition. In some embodiments, a bitter tastant is added simultaneously or sequentially with a compound of the invention. If sequentially, the bitter tastant may be added before or after the compound of the invention. In some embodiments, the edible composition is a food product. In some embodiments, the edible composition is a pharmaceutical composition. In some embodiments, the edible composition is a consumer product.

The amount of both a compound of the present invention and a bitter tastant used in an edible composition depends upon a variety of factors, including the purpose of the composition and the desired or acceptable perception of bitterness, saltiness, or sweetness. The amount may depend on the nature of the edible composition, the particular compound added, the bitter tastant, other compounds present in the composition, the method of preparation (including amount of heat used), and the pH of the edible composition. It will be understood that those of skill in the art will know how to determine the amounts needed to produce the desired taste(s).

In general, a compound of the present invention in an edible composition may be present at a concentration between about 0.001 ppm and 1000 ppm. In some embodiments, the edible composition comprises between about 0.005 to 500 ppm; 0.01 to 100 ppm; 0.05 to 50 ppm; 0.1 to 5 ppm; 0.1 to 10 ppm; 1 to 10 ppm; 1 to 30 ppm; 1 to 50 ppm; 10 to 30 ppm; 10 to 50 ppm; or 30 to 50 ppm of a compound of the present invention. In yet other embodiments, the edible composition comprises about 0.1 to 30 ppm, 1 to 30 ppm or 1 to 50 ppm of a compound of the present invention.

In additional embodiments, the edible composition comprises about 0.1 to 5 ppm; 0.1 to 4 ppm; 0.1 to 3 ppm; 0.1 to 2 ppm; 0.1 to 1 ppm; 0.5 to 5 ppm; 0.5 to 4 ppm; 0.5 to 3 ppm; 0.5 to 2 ppm; 0.5 to 1.5 ppm; 0.5 to 1 ppm; 5 to 15 ppm; 6 to 14 ppm; 7 to 13 ppm; 8 to 12 ppm; 9 to 11 ppm; 25 to 35 ppm; 26 to 34 ppm; 27 to 33 ppm; 28 to 32 ppm; or 29 to 31 ppm.

In yet other embodiments, the edible composition comprises about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, or about 10 ppm of a compound of the present invention. In other embodiments, the edible composition comprises about 1 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, or about 30 ppm of a compound of the present invention.

In still other embodiments, the edible composition comprises about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, or about 50 ppm of a compound of the present invention.

In other embodiments, the edible composition comprises more than about 0.5 ppm, 1 ppm, 5 ppm, 10 ppm, 15 ppm, 20 ppm, 25 ppm, or 30 ppm of a compound of the present invention, up to, for example, about 30 ppm or 50 ppm. In additional embodiments, the edible composition comprises less than about 50 ppm, 30 ppm, 25 ppm, 20 ppm, 15 ppm, 10 ppm, 5 ppm, 1 ppm, or 0.5 ppm of a compound of the present invention. In yet additional embodiments, the edible composition comprises less than about 30 ppm, 10 ppm, or 1 ppm of a compound of the present invention.

When the edible composition comprises KCl, the amount of KCl will vary depending on the nature of the edible composition, the amount of perceived saltiness desired and the presence of other compounds in the composition. In some embodiments, KCl is present at a concentration between about 0.001-15% w/w, 0.001-10% w/w, 0.001-5% w/w; 0.01-5% w/w; 0.1-5% w/w; 1-5% w/w; 0.5-4.8% w/w; 0.5-4% w/w; 0.5-3% w/w; 0.75-3% w/w; 1-2.5% w/w; or 1-2% w/w. In some embodiments, KCl is present at a concentration of about 0.5% w/w, about 1% w/w, about 1.5% w/w, about 2% w/w, about 2.5% w/w, about 3% w/w, about 3.5% w/w, about 4% w/w, about 4.5% w/w, or about 5% w/w. In some embodiments, KCl is present at a concentration of up to about 0.5% w/w, up to about 1% w/w, up to about 1.5% w/w, up to about 2% w/w, up to about 2.5% w/w, up to about 3% w/w, up to about 3.5% w/w, up to about 4% w/w, up to about 4.5% w/w, up to about 5% w/w, up to about 6% w/w, up to about 7% w/w, up to about 8% w/w, up to about 9% w/w, up to about 10% w/w, up to about 11% w/w, up to about 12% w/w, up to about 13% w/w, up to about 14% w/w, or up to about 15% w/w. In some embodiments, KCl is present at a concentration of about 2% w/w.

In some embodiments, KCl is added to the edible composition as a salt substitute in an amount sufficient to replace NaCl. For example, the amount of KCl in the edible compositions may range from about 0.5 to about 1.5 times the replaced NaCl depending upon the application, e.g., if about 0.5 mg of NaCl is replaced, about 0.25 to about 0.75 mg of KCl is added. Typically, KCl is added in the same weight amount as the NaCl being replaced.

Similarly, when the edible composition comprises potassium lactate, the amount of potassium lactate added varies depending on the nature of the edible composition, the amount of preservation required and the presence of other compounds in the composition. Potassium lactate may be present at a concentration between about 0.001-5% w/w; 0.01-5% w/w; 0.1-5% w/w; 0.5-4.8% w/w; 0.5-4% w/w; 0.5-3% w/w; 0.75-3% w/w; 1-2.5% w/w; or 1-2% w/w.

In some embodiments, potassium lactate is added to the edible composition in an amount sufficient to replace sodium lactate. For example, the amount of potassium lactate in the food or beverage after the sodium lactate substitute is added may range from about 0.5 to about 1.5 times the replaced sodium lactate depending upon the application, e.g., if about 0.5 mg of sodium lactate is replaced, about 0.25 to about 0.75 mg of potassium lactate is added. Typically, potassium lactate will be added in the same weight amount as the sodium lactate being replaced.

Further, when the edible composition comprises an artificial sweetener, such as Acesulfame K, the amount of the sweetener added varies depending on the nature of the edible composition, the amount of sweetness required and the presence of other compounds in the composition. Acesulfame K, for example, may be present at a concentration between about 1-200 ppm, 10-200 ppm, 50-150 ppm, 50-125 ppm, 75-125 ppm, and 75-100 ppm, preferably about 75 ppm.

In some embodiments, an artificial sweetener is added to the edible composition in an amount sufficient to replace sugar. In some embodiments, the artificial sweetener has a bitter taste or aftertaste. In some embodiments, the artificial sweetener is Acesulfame K. For example, the amount of Acesulfame K in the edible composition may range from about 0.001 to about 0.01 times the replaced sugar depending upon the application, e.g., if about 100 mg of sugar is replaced, about 0.1 to about 1 mg of Acesulfame K is added. Typically, Acesulfame K will be added in about 0.005 times the amount of sugar being replaced.

In some embodiments, the edible compositions are included in a package. In some embodiments, the edible composition is packaged in bulk, in which the package contains more of the compositions than would typically be used for a single dish or serving of food or beverage. Such bulk packages can be in the form of paper, plastic, or cloth bags or cardboard boxes or drums. Such bulk packages may be fitted with plastic or metal spouts to facilitate the dispensing of the edible composition.

In some embodiments, the package contains an edible composition comprising a compound of the present invention and a bitter tastant. In some embodiments, the package contains an edible composition comprising a compound of the present invention and bitter tasting salt. In some embodiments, the package contains an edible composition comprising a compound of the present invention and a potassium salt, a magnesium salt, or a calcium salt. In some embodiments, the package contains an edible composition comprising a compound of the present invention and a potassium salt. In some embodiments, the package contains an edible composition comprising a compound of the present invention and KCl. In other embodiments, the package contains an edible composition comprising a compound of the present invention and potassium lactate. In some embodiments, the package contains an edible composition comprising a compound of the present invention a potassium salt, and a sodium salt. In other embodiments, the package contains an edible composition comprising a compound of the present invention, KCl and NaCl. In yet other embodiments, the package contains an edible composition comprising a compound of the present invention, potassium lactate and sodium lactate. In other embodiments, the package contains an edible composition comprising a compound of the present invention and Acesulfame K and sugar. In other embodiments, the package contains an edible composition comprising a compound of the present invention, potassium lactate, KCl and NaCl.

In some embodiments, the edible compositions of the present invention are compositions suitable to be used as seasonings, as ingredients in food products or as condiments. In such embodiments, the edible composition may or may not contain a bitter tastant. For example, the edible composition may be used in, e.g., a seasoning which comprises a bitter tastant such as, e.g., KCl. Such seasonings can be used in the place of table salt (i.e., NaCl) to season prepared food products. Alternatively, the edible composition may be used in, e.g., a seasoning which does not contain a bitter tastant. Such seasonings can be used to season prepared food products which contain a bitter tastant (either inherently present or added during preparation) in order to reduce the bitter taste associated with the bitter tastant. In some embodiments, the edible composition is a seasoning comprising KCl and a compound of the invention. In some embodiments, the edible composition is a seasoning comprising KCl, NaCl and a compound of the invention. In some embodiments the seasoning further comprises a spice or a blend of spices.

Alternatively, the edible compositions may be used for medicinal or hygienic purposes, for example, in soaps, shampoos, mouthwash, medicines, pharmaceuticals, cough syrup, nasal sprays, toothpaste, dental adhesives, tooth whiteners, glues (e.g., on stamps and envelopes), and toxins used in insect and rodent control.

Food Product

In some embodiments, the edible composition is a food product. According to such embodiments, the food product comprises (a) a food stuff; and (b) a compound of Formula (I), Formula (II), Formula (III), or Formula (IV), as described herein, or combinations thereof, or any one of Compounds 1-8, as described herein, or combinations thereof.

In some embodiments, the food product further comprises a bitter tastant, as described herein. In some embodiments, the bitter tastant is a potassium salt, such as KCl or potassium lactate. In specific embodiments, the potassium salt is KCl.

In some embodiments, the food product further comprises one or more additional flavor modifiers.

In some embodiments, the food product further comprises one or more additional components selected from the group consisting of preservatives, nutritives, flavorants or additional flavor modifiers, which may lack an inherent flavor.

Pharmaceutical Composition

In some embodiments, the edible composition is a pharmaceutical composition. According to such embodiments, the pharmaceutical composition comprises (a) a bitter tasting pharmaceutically active ingredient; and (b) a compound of Formula (I), Formula (II), Formula (III), or Formula (IV), as described herein, or combinations thereof, or any one of Compounds 1-8, as described herein, or combinations thereof.

According to some embodiments, the pharmaceutical composition can comprise any bitter tasting pharmaceutically active ingredient. Non-limiting examples of bitter pharmaceutical compounds include: acetaminophen, ampicillin, azithromycin, chlorpheniramine, cimetidine, dextromethorphan, diphenhydramine, erythromycin, ibuprofen, penicillin, phenylbutazone, psuedoephedrine, ranitidine, spironolactone, statins (including, but not limited to, atorvastatin, ceirvastatin, fluvastatin, louvastatin, mevastatin, pitavastatin, pravastatin, rosuvastatin, and simvastatin) and theophylline.

In other embodiments, the invention provides a pharmaceutical composition comprising (a) a pharmaceutically active ingredient; (b) a compound of Formula (I), Formula (II), Formula (III), or Formula (IV), as described herein, or combinations thereof, or any one of Compounds 1-8, as described herein, or combinations thereof; and (c) a bitter tastant. In such embodiments, the pharmaceutical compositions may comprise any pharmaceutically active ingredient.

In other embodiments, the invention provides a pharmaceutical composition comprising (a) a pharmaceutically active ingredient; (b) a compound of Formula (I), Formula (II), Formula (III), or Formula (IV), as described herein, or combinations thereof, or any one of Compounds 1-8, as described herein, or combinations thereof; and (c) a potassium salt. In some embodiments, the potassium salt is KCl or potassium lactate. In some embodiments, the potassium salt is KCl.

In some embodiments, the pharmaceutical composition further comprises one or more additional flavor modifiers.

In some embodiments, the pharmaceutical composition further comprises one or more additional components selected from the group consisting of preservatives, nutritives, flavorants or flavor modifiers, which may lack an inherent flavor.

Consumer Product

In some embodiments, the edible compositions is a consumer product. According to such embodiments, the consumer product comprises (a) a bitter tastant; and (b) a compound of Formula (I), Formula (II), Formula (III), or Formula (IV), as described herein, or combinations thereof, or any one of Compounds 1-8, as described herein, or combinations thereof.

In another embodiment, the invention provides a consumer product comprising (a) a potassium salt; and (b) a compound of Formula (I), Formula (II), Formula (III), or Formula (IV), as described herein, or combinations thereof, or any one of Compounds 1-8, as described herein, or combinations thereof. In some embodiments, the potassium salt is KCl or potassium lactate. In some embodiments, the potassium salt is KCl.

In other embodiments, the invention provides a consumer product for reducing bitter taste of a bitter tastant, wherein said consumer product comprises a compound of Formula (I), Formula (II), Formula (III), or Formula (IV), as described herein, or combinations thereof, or any one of Compounds 1-8, as described herein, or combinations thereof. In some embodiments, the bitter tastant is a potassium salt. In some embodiments, the potassium salt is KCl or potassium lactate. In some embodiments, the bitter tastant is KCl.

In some embodiments, the consumer product further comprises one or more additional flavor modifiers.

In some embodiments, the consumer product further comprises one or more additional components selected from the group consisting of preservatives, nutritives, flavorants or additional flavor modifiers, which may lack an inherent flavor.

Method of Preparing an Edible Composition

According to another aspect, the invention provides a method of preparing an edible composition. The method comprises: (a) providing a comestibly acceptable carrier; and (b) adding to the comestibly acceptable carrier of (a) a compound of Formula (I), Formula (II), Formula (III), or Formula (IV), as described herein, or combinations thereof, or any one of Compounds 1-8, as described herein, or combinations thereof, with the comestibly acceptable carrier. In some embodiments, the compound of the invention has been dissolved in a solvent prior to the addition step (b).

In some embodiments, the comestibly acceptable carrier in (a) is inherently bitter. In such embodiments, the comestibly acceptable carrier may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt. In some embodiments, the inherent bitter tastant is KCl. In other embodiments, the inherent bitter tastant is potassium lactate.

In some embodiments, the method of preparing a edible composition further comprises: (c) adding a bitter tastant. In some embodiments, the bitter tastant is a potassium salt. In some embodiments, the potassium salt is KCl or potassium lactate. In specific embodiments, the potassium salt is KCl. In some embodiments, the bitter tastant is added before the compound of the present invention. In other embodiments, the bitter tastant is added after the compound of the present invention. In some embodiments, the compounds of the present invention are combined with the bitter tastant and then combined with the comestibly acceptable carrier. In other embodiments, the compound of the present invention is combined sequentially with the comestibly acceptable carrier and then the bitter tastant. In yet other embodiments, the compounds of the present invention are combined with a mixture of the bitter tastant and the comestibly acceptable carrier.

In some embodiments, a compound of the invention and the bitter tastant, if present, are mixed with the comestibly acceptable carrier. In other embodiments, the compound and the bitter tastant, if present, are sprayed onto or coat the comestibly acceptable carrier. In some embodiments, the compound of the invention is plated on a carbohydrate or salt, encapsulated on a salt or a carbohydrate (spray dried), or co-crystallized with a potassium salt to create a "topping" salt.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the edible composition further comprises a sodium salt. In some embodiments, the edible composition further comprises NaCl. In other embodiments, the edible composition further comprises sodium lactate. In further embodiments, the edible composition further comprises sugar.

In some embodiments, the methods of preparing an edible composition further comprise adding one or more additional components selected from the group consisting of preservatives, nutritives, flavorants or flavor modifiers, which may lack an inherent flavor. In some embodiments, the methods of preparing an edible composition further comprise adding one or more additional flavor modifiers.

In some embodiments, the edible composition is a consumer product.

Method of Preparing a Food Product

According to another aspect, the invention provides a method of preparing an edible composition, wherein the edible composition is a food product. The method comprises: (a) providing a foodstuff; and (b) adding to the foodstuff of (a) a compound of Formula (I), Formula (II), Formula (III), or Formula (IV), as described herein, or combinations thereof, or any one of Compounds 1-8, as described herein, or combinations thereof. In some embodiments, the compound of the invention is added in the form of an edible composition comprising the compound of the invention.

In some embodiments, the foodstuff in (a) is inherently bitter. In such embodiments, the food stuff may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt. In some embodiments, the inherent bitter tastant is KCl. In other embodiments, the inherent bitter tastant is potassium lactate.

In some embodiments, the method comprises: (a) providing a food product; and (b) adding to the food product of (a)

a compound of Formula (I), Formula (II), Formula (III), or Formula (IV), as described herein, or combinations thereof, or any one of Compounds 1-8, as described herein, or combinations thereof. In some embodiments, the compound of the invention is added in the form of an edible composition comprising the compound of the invention.

In some embodiments, the food product in (a) comprises a bitter tastant. In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the method of preparing a food product further comprises: (c) adding a bitter tastant. In some embodiments, the bitter tastant is a potassium salt, such as KCl or potassium lactate. In specific embodiments, the potassium salt is KCl. In some embodiments, the bitter tastant is added before the compound of the present invention. In other embodiments, the bitter tastant is added after the compound of the present invention. In some embodiments, the compound of the invention is added with the bitter tastant. In some embodiments, the compound of the present invention is combined with the bitter tastant and then combined with the foodstuff or food product. In other embodiments, the compound of the present invention is combined sequentially with the foodstuff or food product and then the bitter tastant. In yet other embodiments, the compound of the present invention is combined with a mixture of the bitter tastant and the foodstuff or food product.

In some embodiments, the compound and the bitter tastant, if present, are mixed with the foodstuff. In other embodiments, the compound and the bitter tastant, if present, are sprayed onto or coat the foodstuff. In some embodiments, the compound of the invention is plated on a carbohydrate or salt, encapsulated on a salt or a carbohydrate (spray dried), or co-crystallized with a potassium salt to create a "topping" salt.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the food product further comprises a sodium salt. In some embodiments, the food product further comprises NaCl. In other embodiments, the food product further comprises sodium lactate. In further embodiments, the food product further comprises sugar.

In some embodiments, the methods of preparing a food product further comprise adding one or more additional components selected from the group consisting of preservatives, nutritives, flavorants or flavor modifiers, which may lack an inherent flavor.

Method of Preparing a Pharmaceutical Composition

According to another aspect, the invention provides a method of preparing an edible composition, wherein the edible composition is a pharmaceutical composition. The method comprises: (a) providing a pharmaceutically active ingredient; and (b) adding to the pharmaceutically active ingredient of (a) a compound of Formula (I), Formula (II), Formula (III), or Formula (IV), as described herein, or combinations thereof, or any one of Compounds 1-8, as described herein, or combinations thereof, with the pharmaceutically active ingredient. In some embodiments, the compound of the invention is added in the form of an edible composition comprising the compound of the invention.

In some embodiments, the pharmaceutically active ingredient in (a) is inherently bitter. In such embodiments, the pharmaceutically active ingredient may inherently contain a bitter tastant. In some embodiments, the inherent bitter tastant is a bitter tasting salt. In some embodiments, the inherent bitter tastant is a potassium salt, a magnesium salt, or a calcium salt. In some embodiments, the inherent bitter tastant is a potassium salt.

In some embodiments, the method of preparing a pharmaceutical composition further comprises: (c) adding a bitter tastant. In some embodiments, the bitter tastant is a potassium salt. In some embodiments, the potassium salt is KCl or potassium lactate. In specific embodiments, the potassium salt is KCl. In some embodiments, the bitter tastant is added before the compound of the present invention. In other embodiments, the bitter tastant is added after the compound of the present invention. In some embodiments, the bitter tastant is added with the compound of the invention. In some embodiments, the compound of the present invention is combined with the bitter tastant and then combined with the pharmaceutically active ingredient. In other embodiments, the compound of the present invention is combined sequentially with the pharmaceutically active ingredient and then the bitter tastant. In yet other embodiments, the compound of the present invention is combined with a mixture of the bitter tastant and the pharmaceutically active ingredient.

In some embodiments, the compound and the bitter tastant, if present, are mixed with the pharmaceutically active ingredient. In other embodiments, the compound and the bitter tastant, if present, are sprayed onto or coat the pharmaceutical composition. In some embodiments, the compound of the invention is encapsulated with the pharmaceutically active ingredient. In some embodiments, the compound of the invention is in a form such that the rate of release is regulated vis a vis the rate of release of the bitter tastant, which in some embodiments is the pharmaceutically active ingredient.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate.

In some embodiments, the pharmaceutical composition further comprises a sodium salt. In some embodiments, the pharmaceutical composition further comprises NaCl. In other embodiments, the pharmaceutical composition further comprises sodium lactate. In further embodiments, the pharmaceutical composition further comprises sugar.

In some embodiments, the pharmaceutical composition further comprises a pharmaceutically acceptable carrier. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In some embodiments, the methods of preparing a pharmaceutical composition further comprise adding one or more additional components selected from the group consisting of preservatives, nutritives, flavorants or flavor modifiers, which may lack an inherent flavor.

Method of Reducing or Eliminating the Perception of Bitter Taste in a Subject

According to another aspect, the invention provides a method of reducing or eliminating the perception of bitter taste in a subject. The method comprises the use of an edible composition comprising a compound according to Formula (I), Formula (II), Formula (III), or Formula (IV), as described herein, or combinations thereof, or any one of Compounds 1-8, as described herein, or combinations thereof.

The method can be used to reduce or eliminate bitter taste in any edible composition, including a foodstuff, food product, pharmaceutical composition or consumer product. The edible composition may be in any form. In some embodiments, the composition is in the form of, for example, a gum, lozenge, sauce, condiment, meat matrix, meat slurry, paste, suspension, spread, coating, a liquid, a gel, an emulsion, granules, or seasoning.

In some embodiments the edible composition is utilized by, for example, placement in the oral cavity or by ingestion. In some embodiments, the edible composition is placed in the oral cavity or ingested before a bitter food stuff, food product, pharmaceutical composition or consumer product. In some embodiments, the edible composition is placed in the oral cavity or ingested concurrently with a bitter food stuff, food product, pharmaceutical composition or consumer product, either as a separate edible composition or by incorporation in the bitter food stuff, food product, pharmaceutical composition or consumer product. In some embodiments, the edible composition is placed in the oral cavity or ingested after a bitter food stuff, food product, pharmaceutical composition or consumer product. For example, a compound of the invention can be combined with foodstuffs or food products to reduce the bitter taste of a food product. Alternatively, a compound of the invention can be used, for example, in a lozenge or gum for use after exposure to a bitter food stuff, food product, pharmaceutical composition or consumer product (e.g., to reduce or eliminate a bitter aftertaste).

Method of Reducing the Amount of Sodium in an Edible Composition

According to another embodiment, the invention provides a method of reducing the amount of sodium in an edible composition, such as a food product, a pharmaceutical composition or a consumer product. In some embodiments, the invention provides a method of reducing the amount of a sodium containing compound in an edible composition, such as a food product, a pharmaceutical composition or a consumer product. In another embodiment, the invention provides a method of reducing the amount of NaCl in an edible composition, such as a food product, a pharmaceutical composition or a consumer product. In another embodiment, the invention provides a method of reducing the amount of sodium lactate in an edible composition, such as a food product, a pharmaceutical composition or a consumer product. In some embodiments, the sodium salt is replaced with a non-sodium salt. In some embodiments, the non-sodium salt is a calcium salt, a magnesium salt, or a potassium salt. In some embodiments, the non-sodium salt is a potassium salt.

In some embodiments, the method comprises: (a) replacing an amount of a sodium salt used in preparing an edible composition with an amount of a potassium salt; and (b) incorporating into the edible composition an effective amount of a compound of Formula (I), Formula (II), Formula (III), or Formula (IV), as described herein, or combinations thereof, or any one of Compounds 1-8, as described herein, or combinations thereof. In some embodiments, the compound of the invention is added in the form of an edible composition comprising the compound of the invention.

In some embodiments, the method of reducing the amount of sodium in an edible composition comprises the steps of: (a) ingesting a first edible composition, in which an amount of a sodium salt has been replaced with an amount of a potassium salt; and (b) ingesting a second edible compound, which comprises a compound of the invention. In some embodiments, the first edible composition is ingested before the second edible composition. In some embodiments, the first edible composition is ingested after the second edible composition. In some embodiments, the first edible composition is ingested concurrently with the second edible composition.

In some embodiments, the edible composition is a food product. In some embodiments, the edible composition is a pharmaceutical composition. In some embodiments, the edible composition is a consumer product.

In some embodiments, the potassium salt is added to the edible composition prior to addition of an effective amount of a compound of the invention. In some embodiments, the potassium salt is added to the edible composition subsequent to addition of an effective amount of a compound of the invention. In some embodiments, the potassium salt is added to the edible composition concurrent with addition of an effective amount of a compound of the invention.

In some embodiments, the amount of sodium replaced in the edible composition in step (a) is an amount sufficient to maintain or restore the health of a subject. In some embodiments, the amount of sodium replaced in the edible composition is an amount sufficient to decrease hypertension in a subject. In some embodiments, the amount of sodium replaced by potassium in the edible composition is an amount sufficient to change the texture or freezing point of the edible composition. In some embodiments, the amount of sodium replaced is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in step (b) reduces the perception of bitter taste in the subject. The bitter taste is completely reduced or partially reduced. In some embodiments, the perception of salty taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100% of the amount of sodium present in the edible composition with potassium. These amounts are not meant to be limiting, and increments between the recited percentages are specifically envisioned as part of the invention. In some embodiments, the amount of compound added in step (b) is sufficient to permit replacement of up to 25% of the amount of sodium present in the edible composition with potassium. In other embodiments, the amount of compound added in step (b) is sufficient to permit replacement of up to 50% of the amount of sodium present in the edible composition with potassium. In other embodiments, the amount of compound added in step (b) is sufficient to permit replacement of up to 75% of the amount of sodium present in the edible composition with potassium. In yet other embodiments, the amount of compound added in step (b) is sufficient to permit replacement of up to 100% of the amount of sodium present in the edible composition with potassium.

In some embodiments, the method of reducing the amount of sodium in an edible composition further comprises adding one or more additional components selected from the group consisting of preservatives, nutritives, flavorants or flavor modifiers, which may lack an inherent flavor.

In some embodiments, the method comprises: (a) replacing an amount of NaCl used in preparing an edible composition with an amount of KCl; and (b) incorporating into the edible composition an effective amount of a compound of Formula (I), Formula (II), Formula (III), or Formula (IV), as described herein, or combinations thereof, or any one of Compounds 1-8, as described herein, or combinations thereof.

In some embodiments, the method of reducing the amount of sodium in an edible composition comprises the steps of: (a) ingesting a first edible composition, in which an amount of NaCl has been replaced with an amount of KCl; and (b) ingesting a second edible compound, which comprises a compound of the invention. In some embodiments, the first edible composition is ingested before the second edible composition. In some embodiments, the first edible composition is ingested after the second edible composition. In some embodiments, the first edible composition is ingested concurrently with the second edible composition.

In some embodiments, the edible composition is a food product. In some embodiments, the edible composition is a pharmaceutical composition. In some embodiments, the edible composition is a consumer product.

In some embodiments, the KCl is added to the edible composition prior to addition of an effective amount of a compound of the invention. In some embodiments, the KCl is added to the edible composition subsequent to addition of an effective amount of a compound of the invention.

In some embodiments, the KCl is added to the edible composition concurrent with addition of an effective amount of a compound of the invention.

In some embodiments, the amount of NaCl replaced by KCl in the edible composition in step (a) is an amount sufficient to maintain or restore the health of a subject. In some embodiments, the amount of NaCl replaced by KCl in the edible composition is an amount sufficient to decrease hypertension in a subject. In some embodiments, the amount of NaCl replaced by KCl in the edible composition is an amount sufficient to change the texture or freezing point of the edible composition. In some embodiments, the amount of NaCl replaced by KCl is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in step (b) reduces the perception of bitter taste in the subject. The bitter taste is completely reduced or partially reduced. In some embodiments, the perception of salty taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100% of the amount of NaCl present in the edible composition with KCl. These amounts are not meant to be limiting, and increments between the recited percentages are specifically envisioned as part of the invention. In some embodiments, the amount of compound added in step (b) is sufficient to permit replacement of up to 25% of the amount of NaCl present in the edible composition with KCl. In other embodiments, the amount of compound added in step (b) is sufficient to permit replacement of up to 50% of the amount of NaCl present in the edible composition with KCl. In other embodiments, the amount of compound added in step (b) is sufficient to permit replacement of up to 75% of the amount of NaCl present in the edible composition with KCl. In yet other embodiments, the amount of compound added in step (b) is sufficient to permit replacement of up to 100% of the amount of NaCl present in the edible composition with KCl.

In some embodiments, the method of reducing the amount of NaCl in an edible composition or food product comprises maintaining a salty flavor.

In some embodiments, the method of reducing the amount of NaCl in an edible composition further comprises adding one or more additional components selected from the group consisting of preservatives, nutritives, flavorants or flavor modifiers, which may lack an inherent flavor.

In other embodiments, the method of reducing the amount of sodium in an edible composition comprises: (a) replacing an amount of sodium lactate present in the edible composition with an amount of potassium lactate; and (b) incorporating into the edible composition an effective amount of a compound of Formula (I), Formula (II), Formula (III), or Formula (IV), as described herein, or combinations thereof, or any one of Compounds 1-8, as described herein, or combinations thereof.

In some embodiments, the method of reducing the amount of sodium in an edible composition comprises the steps of: (a) ingesting a first edible composition, in which an amount of sodium lactate has been replaced with an amount of potassium lactate; and (b) ingesting a second edible compound, which comprises a compound of the invention. In some embodiments, the first edible composition is ingested before the second edible composition. In some embodiments, the first edible composition is ingested after the second edible composition. In some embodiments, the first edible composition is ingested concurrently with the second edible composition.

In some embodiments, the edible composition is a food product. In some embodiments, the edible composition is a pharmaceutical composition. In some embodiments, the edible composition is a consumer product.

In some embodiments, the potassium lactate is added to the edible composition prior to addition of an effective amount of a compound of the invention. In some embodiments, the potassium lactate is added to the edible composition subsequent to addition of an effective amount of a compound of the invention. In some embodiments, the potassium lactate is added to the edible composition concurrent with addition of an effective amount of a compound of the invention.

In some embodiments, the amount of sodium lactate replaced by potassium lactate in the edible composition in step (a) is an amount sufficient to maintain or restore the health of a subject. In some embodiments, the amount of sodium lactate replaced by potassium lactate in the edible composition is an amount sufficient to decrease hypertension in a subject. In some embodiments, the amount of sodium lactate replaced by potassium lactate in the edible composition is an amount sufficient to change the texture or freezing point of the edible composition. In some embodiments, the amount of sodium lactate replaced by potassium lactate is up to 1%, 2%, 3%, 4%, 5%, 6%, 7%, 8%, 9%, 10%, 15%, 20%, 25%, 30%, 35%, 40%, 45%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in step (b) reduces the perception of bitter taste in the subject. The bitter taste is completely reduced or partially reduced. In some embodiments, the perception of salty taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100% of the amount of sodium lactate present in the edible composition with potassium lactate. These amounts are not meant to be limiting, and increments between the recited percentages are specifically envisioned as part of the invention. In some embodiments, the amount of compound added in step (b) is sufficient to permit replacement of up to 25% of the amount of sodium lactate present in the edible composition with potassium lactate. In other embodiments, the amount of compound added in step (b) is sufficient to permit replacement of up to 50% of the amount of sodium lactate present in the edible composition with potassium lactate. In other embodiments, the amount of compound added in step (b) is sufficient to permit replacement of up to 75% of the amount of sodium lactate present in the edible composition with potassium lactate. In yet other embodiments, the amount of compound added in step (b) is sufficient to permit replacement of up to 100% of the amount of sodium lactate present in the edible composition with potassium lactate.

In some embodiments, the method of reducing the amount of sodium lactate in an edible composition or food product comprises maintaining the preservation of the food product.

In some embodiments, the method of reducing the amount of sodium lactate in an edible composition further comprises adding one or more additional components selected from the group consisting of preservatives, nutritives, flavorants or flavor modifiers, which may lack an inherent flavor.

Method of Reducing the Amount of Sugar in an Edible Composition or Food Product

According to another embodiment, the invention provides a method of reducing the amount of sugar in an edible composition. In some embodiments, the method comprises: (a) replacing an amount of sugar used in preparing an edible composition with an amount of Acesulfame K; and (b) incorporating into the edible composition an effective amount of a compound of Formula (I), Formula (II), Formula (III), or Formula (IV), as described herein, or combinations thereof, or any one of Compounds 1-8, as described herein, or combinations thereof.

In some embodiments, the edible composition is a food product. In some embodiments, the edible composition is a pharmaceutical composition. In some embodiments, the edible composition is a consumer product.

In some embodiments, the Acesulfame K is added to the edible composition prior to addition of an effective amount of a compound of the invention. In some embodiments, the Acesulfame K is added to the edible composition subsequent to addition of an effective amount of a compound of the invention. In some embodiments, the Acesulfame K is added to the edible composition concurrent with addition of an effective amount of a compound of the invention.

In some embodiments, the amount of sugar replaced in the edible composition in (a) is an amount sufficient to maintain or restore the health of a subject. In some embodiments, the amount of sugar replaced in the edible composition is an amount sufficient to result in weight loss in a subject. In some embodiments, the amount of sugar replaced by Acesulfame K in the edible composition is an amount sufficient to alleviate the effects of, or treat, a disease associated with sugar consumption or excessive weight of the subject (e.g., diabetes). In some embodiments, the amount of sugar replaced by Acesulfame K is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention.

In some embodiments, the amount of compound added in (b) reduces the perception of bitter taste in the subject. The bitter taste is completely reduced or partially reduced. In some embodiments, the perception of sweet taste is maintained.

In some embodiments, the amount of compound added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100% of the amount of sugar present in the edible composition with Acesulfame K. These amounts are not meant to be limiting, and increments between the recited percentages are specifically envisioned as part of the invention. In some embodiments, the amount of compound added in step (b) is sufficient to permit replacement of up to 25% of the amount of sugar present in the edible composition with Acesulfame K. In other embodiments, the amount of compound added in step (b) is sufficient to permit replacement of up to 50% of the amount of sugar present in the edible composition with Acesulfame K. In other embodiments, the amount of compound added in step (b) is sufficient to permit replacement of up to 75% of the amount of sugar present in the edible composition with Acesulfame K. In yet other embodiments, the amount of compound added in step (b) is sufficient to permit replacement of up to 100% of the amount of sugar present in the edible composition with Acesulfame K.

In some embodiments, the method of reducing the amount of sugar in an edible composition comprises maintaining a sweet flavor.

In some embodiments, the method of reducing the amount of sugar in an edible composition or food product further comprises adding one or more additional components selected from the group consisting of preservatives, nutritives, flavorants or flavor modifiers, which may lack an inherent flavor.

Method of Reducing Sodium Intake of a Subject

According to another embodiment, the invention provides a method of reducing sodium intake of a subject. In some embodiments, the method comprises the step of providing an edible composition of the present invention to the subject, wherein all or a portion of the sodium salts in the edible composition is replaced with one or more non-sodium salts, and wherein the edible composition comprises a compound of the present invention. In some embodiments, the non-sodium salt is a calcium salt, a magnesium salt, or a potassium salt. In some embodiments, the non-sodium salt is a potassium salt. In some embodiments, the edible composition is a food product. In some embodiments, the edible composition is a pharmaceutical composition. In some embodiments, the edible composition is a consumer product. In some embodiments the sodium salt is NaCl and the potassium salt is KCl. In some embodiments, the sodium salt is sodium lactate and the potassium salt is potassium lactate.

In some embodiments, the methods of reducing sodium intake of a subject further comprise the step of identifying a subject in need thereof. The skilled worker would be able to identify a subject in need of reducing sodium intake. Non-limiting examples of such subjects include subjects that suffer from any one or more of the following disorders: hypernatremia, hypertension, cardiovascular disease, edema, seizures due to cerebral edema, dehydration (due to excess sweating, diarrhea, urinary tract disorders or diuretics), diabetes insipidus, Conn's syndrome, and Cushing's syndrome.

In some embodiments, the amount of the sodium salt replaced by a potassium salt in the edible composition is an amount sufficient to maintain or restore the health of a subject. In some embodiments, the amount of the sodium salt replaced by a potassium salt in the edible composition is an amount sufficient to decrease hypertension in a subject. In some embodiments, the amount of the sodium salt replaced by a potassium salt in the edible composition is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, a subject's daily sodium intake is less than 2500 mg/day, less than 2000 mg/day, less than 1500 mg/day, less than 1000 mg/day, or less than 500 mg/day, where desirable.

In some embodiments, the amount of the compound of the invention added to the edible composition is sufficient to permit reduction of a subject's sodium intake by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the amount of compound of the invention added to the edible composition is sufficient to permit reduction of the subject's sodium intake by up to 25%. In other embodiments, the amount of compound of the invention added to the edible composition is sufficient to permit reduction of the subject's sodium intake by up to 50%. In other embodiments, the amount of compound of the invention added to the edible composition is sufficient to permit reduction of the subject's sodium intake by up to 75%. In yet other embodiments, the amount of compound of the invention added to the edible composition is sufficient to permit reduction of the subject's sodium intake by up to 100%.

In some embodiments, the method of reducing sodium intake of a subject further comprises adding one or more additional components selected from the group consisting of preservatives, nutritives, flavorants or flavor modifiers, which may lack an inherent flavor.

Method of Reducing Sugar Intake of a Subject

According to another embodiment, the invention provides a method of reducing sugar intake of a subject. In some embodiments, the method comprises the step of providing an edible composition of the present invention to the subject, wherein all or a portion of the sugar in the edible composition is replaced with Acesulfame K, and wherein the edible composition comprises a compound of the present invention. In some embodiments, the edible composition is a food product. In some embodiments, the edible composition is a pharmaceutical composition. In some embodiments, the edible composition is a consumer product.

In some embodiments, the methods of reducing sugar intake of a subject further comprise the step of identifying a subject in need thereof. The skilled worker would be able to identify a subject in need of reducing sugar intake. Non-limiting examples of such subjects include subjects that suffer from any one or more of the following disorders: diabetes, pre-diabetes, insulin resistance, obesity, excessive weight, and hyperglycemia.

In some embodiments, the amount of sugar replaced by Acesulfame K in the edible composition is an amount sufficient to maintain or restore the health of a subject. In some embodiments, the amount of sugar replaced by Acesulfame K in the edible composition is an amount sufficient to result in weight loss in a subject. In some embodiments, the amount of sugar replaced by Acesulfame K in the edible composition is an amount sufficient to alleviate the effects of, or treat, a disease associated with sugar consumption or excessive weight of the subject (e.g., diabetes). In some embodiments, the amount of sugar replaced by Acesulfame K in the edible composition is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the subject's daily sugar intake is less than 250 g/day, less than 200 g/day, less than 175 g/day, less than 150 g/day, less than 125 g/day, less than 100 g/day, less than 75 g/day, less than 50 g/day or less than 25 g/day.

In some embodiments, the amount of compound of the invention added to the edible composition is sufficient to permit reduction of a subject's sugar intake by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the amount of compound of the invention added to the edible composition is sufficient to permit reduction of a subject's sugar intake by up to 25%. In other embodiments, the amount of compound of the invention added to the edible composition is sufficient to permit reduction of a subject's sugar intake by up to 50%. In other embodiments, the amount of compound of the invention added to the edible composition is sufficient to permit reduction of a subject's sugar intake by up to 75%. In yet other embodiments, the amount of compound of the invention added to the edible composition is sufficient to permit reduction of a subject's sugar intake by up to 100%.

In some embodiments, the method of method of reducing sugar intake of a subject further comprises adding one or more additional components selected from the group consisting of preservatives, nutritives, flavorants or flavor modifiers, which may lack an inherent flavor.

Method of Reducing Bitter Taste of an Edible Composition

According to another embodiment, the invention provides methods of reducing the bitter taste in an edible composition. In some embodiments, the edible composition is a food product. In some embodiments, the edible composition is a pharmaceutical composition. In some embodiments, the edible composition is a consumer product.

In one embodiment, the method comprises: (a) adding an effective amount of a compound of Formula (I), Formula (II), Formula (III), or Formula (IV), as described herein, or combinations thereof, or any one of Compounds 1-8, as described herein, or combinations thereof, to an edible composition such that bitter taste is reduced.

In alternate embodiments, the method comprises: (a) ingesting an effective amount of a compound of Formula (I), Formula (II), Formula (III), or Formula (IV), as described herein, or combinations thereof, or any one of Compounds 1-8, as described herein, or combinations thereof, before, along with, or after the edible composition such that bitter taste is reduced.

In some embodiments, the bitter tastant is a bitter tasting salt. In some embodiments, the bitter tastant is a potassium salt, a magnesium salt, or a calcium salt. In some embodiments, the bitter tastant is a potassium salt. In some embodiments, the bitter tastant is KCl. In other embodiments, the bitter tastant is potassium lactate. In some embodiments, the bitter tastant is inherent in the edible composition, such as in an inherently bitter foodstuff.

In some embodiments, the bitter taste is reduced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the bitter taste is reduced by up to 25%. In other embodiments, the bitter taste is reduced by up to 50%.

In other embodiments, the bitter taste is reduced by up to 75%. In other embodiments, the bitter taste is reduced by up to 100%.

In some embodiments, the method of reducing the bitter taste attributed to a bitter tastant in an edible composition further comprises adding one or more additional components selected from the group consisting of preservatives, nutritives, flavorants or flavor modifiers (which lack an inherent flavor).

Method of Preserving an Edible Composition

According to another embodiment, the invention provides a method of preserving an edible composition an edible composition comprising:
(a) providing an edible composition; and
(b) combining with the edible composition of (a) a preservative and an effective amount of a compound of Formula (I), Formula (II), Formula (III), or Formula (IV), as described herein, or combinations thereof.

In another embodiment, the method of preserving an edible composition comprises:
(a) providing an edible composition; and
(b) combining with the edible composition of (a) a preservative and an effective amount of any one of Compounds 1-8, as described herein, or combinations thereof.

According to the invention, the preservative can be any bitter-tasting preservative. In some embodiments, the preservative in (a) is a potassium salt. In some embodiments, the preservative in (a) is potassium lactate.

In some embodiments, the edible composition is a food product. In some embodiments, the edible composition is a pharmaceutical composition. In some embodiments, the edible composition is a consumer product.

In some embodiments, the method of preserving an edible composition further comprises adding one or more additional components selected from the group consisting of preservatives, nutritives, flavorants or flavor modifiers, which may lack an inherent flavor.

Method of Reducing the Amount of Sodium in an Edible Composition while Preserving the Edible Composition According to another embodiment, the invention provides a method of reducing the amount of sodium in an edible composition while preserving the edible composition. In some embodiments, the method comprises replacing an amount of sodium containing preservative used in preparing an edible composition with an amount of potassium containing preservative and adding an effective amount of a compound of Formula (I), Formula (II), Formula (III), or Formula (IV), as described herein, or combinations thereof, or any one of Compounds 1-8, as described herein, or combinations thereof.

In some embodiments, the method comprises replacing an amount of sodium lactate used in preparing an edible composition with an amount of potassium lactate and adding an effective amount of a compound of Formula (I), Formula (II), Formula (III), or Formula (IV), as described herein, or combinations thereof, or any one of Compounds 1-8, as described herein, or combinations thereof.

In some embodiments, the edible composition is a food product. In some embodiments, the edible composition is a pharmaceutical composition. In some embodiments, the edible composition is a consumer product.

In some embodiments, the effective amount of the compound is sufficient to permit reduction of the amount of sodium lactate typically used in preparing an edible composition by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. These amounts are not meant to be limiting, and increments between the recited percentages are specifically envisioned as part of the invention. In some embodiments, the effective amount of the compound is sufficient to permit reduction of the amount of sodium lactate typically present in an edible composition by up to 25%. In other embodiments, the effective amount of the compound is sufficient to permit reduction of the amount of sodium lactate typically present in an edible composition by up to 50%. In other embodiments, the effective amount of the compound is sufficient to permit reduction of the amount of sodium lactate typically present in an edible composition by up to 75%. In yet other embodiments, the effective amount of the compound is sufficient to permit reduction of the amount of sodium lactate typically present in an edible composition by up to 100%.

In some embodiments, the method of reducing the bitter taste attributed to a bitter tastant in an edible composition further comprises adding one or more additional components selected from the group consisting of preservatives, nutritives, flavorants or flavor modifiers, which may lack an inherent flavor. In some embodiments, the method of reducing the amount of sodium lactate in an edible composition while preserving the food product further comprises adding one or more additional flavor modifiers.

Method of Inhibiting a Bitter Taste Receptor

According to another embodiment, the invention provides a method of inhibiting or reducing activation and/or signaling of a bitter taste receptor. In some embodiments, the method comprises contacting a bitter taste receptor with a compound according to Formula (I), Formula (II), Formula (III), or Formula (IV), as described herein, or combinations thereof, or any one of Compounds 1-8, as described herein, or combinations thereof.

In some embodiments, the method comprises contacting a bitter taste receptor with an edible composition comprising a compound according to Formula (I), Formula (II), Formula (III), or Formula (IV), as described herein, or combinations thereof, or any one of Compounds 1-8, as described herein, or combinations thereof.

In some embodiments, the edible composition is a food product. In some embodiments, the edible composition is a pharmaceutical composition. In some embodiments, the edible composition is a consumer product.

In some embodiments, the bitter taste receptor is an ex vivo receptor present in, for example, an assay. In some embodiments, the bitter taste receptor is an in vitro receptor present in, for example, an assay. In other embodiments, the bitter taste receptor is an in vivo receptor present in a subject. In some embodiments, the bitter taste receptor is present in the oral cavity or gastrointestinal tract of a subject. In some embodiments, the bitter receptor is in the oral cavity of a human. In some embodiments, the bitter receptor is in the oral cavity of a non-human animal. In some embodiments, the bitter receptor is in the oral cavity of an animal model.

In some embodiments, inhibition of a bitter taste receptor will affect a physiological process or condition. Non-limiting examples of physiological processes and conditions affected by inhibition of bitter taste receptors include bitter taste, hypertension, nausea, emesis, effects on the gastrointestinal tract, appetite, nutrition, nutrient absorption, satiety, hunger, diabetes, obesity, blood glucose levels, blood glucose regulation, metabolism, diet, and eating disorders.

Preparation of the Compounds of the Invention

In some embodiments, one or more of the compounds of Formula (I), Formula (II), Formula (III), or Formula (IV) are commercially available, for example from commercial sources such as Sigma-Aldrich® of St. Louis, Mo., USA; TCI America, Portland, Oreg., USA; and Acros Organics, Geel, Belgium; among others.

In other embodiments, one or more of the compounds of Formula (I), Formula (II), Formula (III), or Formula (IV) are prepared from commercially available reagents by routine methods in synthetic organic chemistry.

Compounds of Formula (I)

In one embodiment, one or more compounds of Formula (I) are prepared by the multi-step sequence described below. One of skill in the art would be able to readily adapt the described conditions for the synthesis of any of the compounds of Formula (I).

The synthesis of phytol can be accomplished beginning with methylalumination (AlMe$_3$) of alkene A1 followed by exposure to I$_2$ to generate iodoalkene A2. A2 may then be coupled with 3-butenylmagnesium bromide to afford alkene A3. Such couplings may be accomplished using copper catalysts such as, for example, Li$_2$CuCl$_4$. A3 may be converted to A4 using conditions similar to those used in the A1 to A2 conversion—i.e., by methylalumination followed by exposure to I$_2$. A4 may be cross-coupled with 4-trimethylsilyl-3-butynylmagnesium bromide followed by desilylation to yield A5. Such cross-couplings may be accomplished using copper catalysts such as, for example, Li$_2$CuCl$_4$. Such desilylation reactions may be accomplished using, for example, methanolic KOH. A5 may then be converted to phytol via methylalumination, complexation with n-BuLi, and treatment with (CH$_2$O)$_n$ (Scheme I):

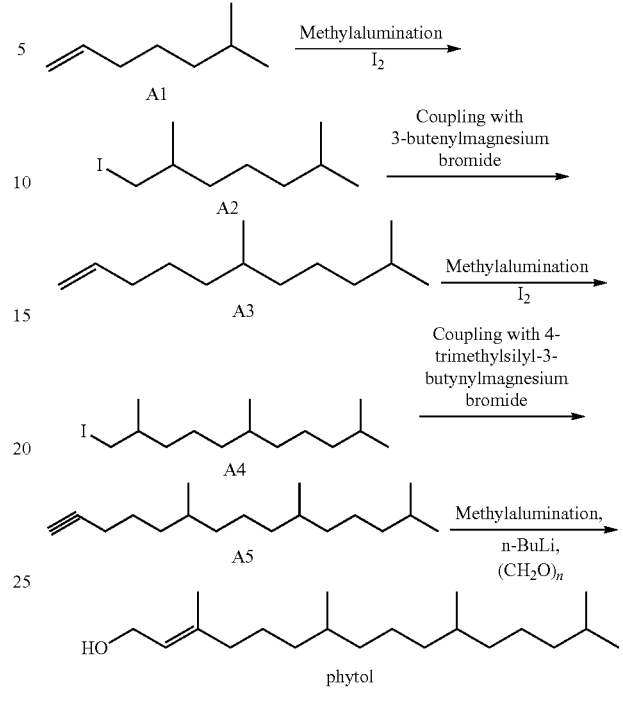

The enantioselective syntheses of phytol and phytol-like compounds are described in, for example, Shouquan Huo et al., *Organic Letters*, 3(21):3253-3256 (2001), which is hereby incorporated by reference.

Compounds of Formula (II)

The compounds of Formula (II) may be prepared in general by methods known to those skilled in the art. Scheme II below illustrates synthetic routes to the compounds of Formula (II). Other equivalent schemes, which will be readily apparent to the ordinary skilled organic chemist, may alternatively be used to synthesize various portions of the molecules as illustrated by general schemes below.

The synthesis of Formula (II) compounds can be accomplished beginning with condensation of A6 and A7 catalyzed by a Zn catalyst, such as zinc chloride, to generate A8. A8 may be converted to A9 via NaBH$_4$/CeCl$_3$ mediated reduction followed by treatment of Ac$_2$O. A9 to A10 conversion may be achieved by treatment of A9 with 1,8-Diazabicyclo[5.4.0]undec-7-ene (DBU). A10 may be treated with a lithium reagent, R$_2$.Li, to generate compounds of Formula (II), where R$_2$ is a C$_1$-C$_6$ alkyl, C$_2$-C$_6$ alkenyl, or C$_2$-C$_6$ alkynyl group. Alternatively, A10 may be treated with Diisobutylaluminium hydride (DIBAL-H) to generate compounds of Formula (II), where R$_2$ is H.

In one embodiment, one or more compounds of Formula (II) can be prepared according to Scheme II.

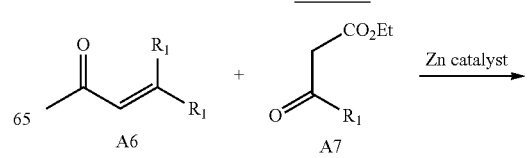

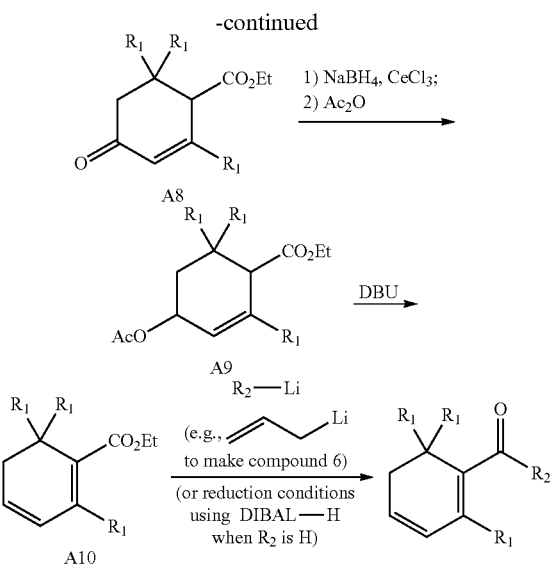

Compounds of Formula (III)

In one embodiment, one or more compounds of Formula (III) is prepared by acylation of alcohol A11 with acyl compound A12 bearing leaving group LG to afford product A13 (Scheme III):

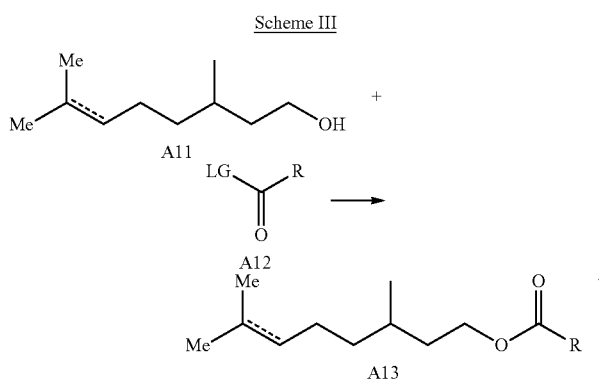

Suitable leaving groups include those recognized in the art for acylation reactions, such as halide (e.g., chloro, bromo, iodo), aryloxy, leaving groups associated with activated esters (e.g., N-succinamide or that associated with dicyclohexylcarbodiimide), and the like. In certain embodiments, acyl compound A7 is an acid anhydride; that is LG is —OC(O)R. In some embodiments, acylation conditions also employ an inorganic or organic base. Suitable bases include those recognized in the art for such reactions, and include but are not limited to alkaline and alkaline earth metal carbonates (such as $Na_2CO_3$, $K_2CO_3$, $CaCO_3$, etc.) and bicarbonates (such as $NaHCO_3$, $KHCO_3$, etc.). Other suitable bases include amine bases, such as ammonia, ammonium hydroxide, triethylamine, pyridine, piperidine, pyrrolidine, 2,6-lutidine, 1,8-diazabicycloundec-7-ene (DBU), 4-(dimethylamino)-pyridine, etc.

In one particular embodiment, A12 is an acid halide, such as an acid chloride or bromide, and the acylation reaction proceeds in the presence of an amine base, such as triethylamine, pyridine, piperidine, pyrrolidine, 2,6-lutidine, 1,8-diazabicycloundec-7-ene (DBU), 4-(dimethylamino)-pyridine, etc.

In another embodiment, A12 is an activated ester and acylation proceeds under mild conditions that do not result in the generation of strong acids.

A12 can be prepared from the corresponding carboxylic acid using routine methods known in the art.

Compounds of Formula (IV)

The compounds of Formula (IV) may be prepared in general by methods known to those skilled in the art. Scheme IV below illustrates synthetic routes to the compounds of Formula (IV). Other equivalent schemes, which will be readily apparent to the ordinary skilled organic chemist, may alternatively be used to synthesize various portions of the molecules as illustrated by general schemes below.

The synthesis can be accomplished beginning with treatment of A15 with NaH, followed by addition of absolute EtOH and A14, to generate A16. A16 may be converted to A17 via Raney Ni catalyzed reduction. A17 can then be treated with oxalyl chloride to generate acyl chloride A18. A18 may be treated with a lithium cuprate reagent, $(R_2)_2$CuLi, to generate compounds of Formula IV, where $R_2$ is a $C_1$-$C_6$ alkyl, $C_2$-$C_6$ alkenyl, or $C_2$-$C_6$ alkynyl group. Alternatively, A18 may be treated with $LiAl(O\text{-}t\text{-}Bu)_3H$ to generate compounds of Formula IV, where $R_2$ is H (Scheme IV):

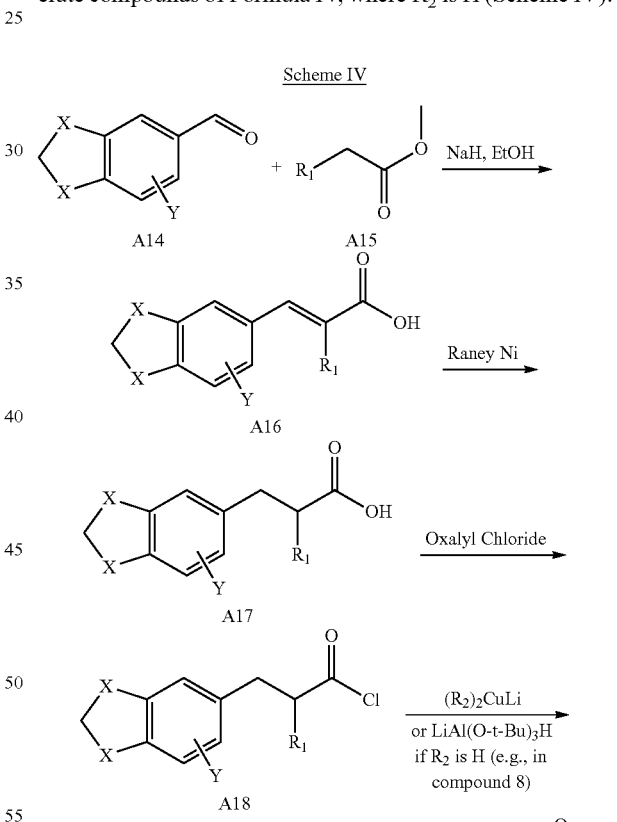

EXAMPLES

In order that this invention be more fully understood, the following examples are set forth. These examples are for the purpose of illustration only and are not to be construed as limiting the scope of the invention in any way.

The test compounds used in the following examples may be obtained from commercial vendors for synthetic and natural compounds, such as VitasM, ChemDiv, Chem-Bridge, Chromadex, Sigma Aldrich, Penta, Spectrum Chemical, Vigon, and Indofine.

The taste test panelists used in the following examples were screened based upon and selected for their ability to perceive the bitter taste associated with potassium chloride. Only panelists capable of perceiving bitter taste participated in the following taste tests.

Due to the complex nature of taste perception in subjects and the inherently subjective nature of the following experiments, individual taste test trials may yield different results for a given compound. The data presented in the following Examples is illustrative of the taste testing results observed.

The taste testing experiments below were conducted with panels of varying size (i.e., panels comprising varying numbers of panelists).

Example 1 Effect of Test Compounds on the Perception of Bitter Taste of KCl Solid-Matrix Foodstuffs in Humans Using a Latin Square Two-Alternative Forced Choice Method (Latin Square-2AFC)

The effect of the test compounds on the perception of the bitter taste of KCl in solid-matrix foodstuffs in humans was evaluated using a "chew and spit" test using a Latin Square-2AFC testing method as follows.

Two types of marinades containing Prague powder, sugar, Evian™ water, KCl and/or NaCl in water were prepared. One marinade contained 80% KCl:20% NaCl (by weight) (i.e., marinade concentration of about 10.9% KCl to give a KCl concentration of about 1.6% in the final food product). A second marinade contained 60% KCl:40% NaCl (by weight) (i.e., marinade concentration of about 8.2% KCl to give a KCl concentration of about 1.2% in the final food product). Compound stock solutions were prepared by dissolving an amount of test compound in ethanol or water (depending on the solubility of the compound) to create a 5 mg/mL stock compound solution. Enough ethanol was added to each stock compound solution to generate a final stock compound solution containing 1% ethanol. The marinade, the stock compound solution and ground turkey were added to a mixing bowl, mixed at low-speed for about 2 minutes, and then mixed at high-speed for about 5 minutes. The marinated turkey mixture was divided into one pound aliquots, vacuum sealed into food saver bags, and allowed to marinate for about 2 hours in a refrigerator. The vacuum-sealed turkey was then cooked in an about 86° C. water bath for about 30 minutes. If after about 30 minutes, the internal turkey temperature had not reached about 170° F., the vacuum-sealed turkey was cooked for about an additional 5 minutes. The vacuum-sealed turkey was then refrigerated for about two weeks before taste testing. KCl standards were similarly prepared by dissolving KCl in the marinade without adding any test compound during the turkey preparation. NaCl standards were similarly prepared by dissolving NaCl in the marinade without adding any test compound during the turkey preparation (NaCl standards did not contain any KCl).

The panelists tasted portions by chewing and spitting. In order to eliminate any effects of sample order, a complete Latin Square design was employed so that each possible order of sample presentation was utilized across subjects. Each sample was tested in several discrete taste test experiments. Panelists were asked to rinse with Poland Spring™ water, eat a cracker, and wait about 10 minutes between samples. In each case, the panelists were asked to choose the sample that tasted less bitter. Illustrative results presented in FIG. 1.

Example 2 Effect of Test Compounds on the Perception of Bitter Taste of KCl Food Product in Humans Using a Latin Square Two-Alternative Forced Choice Method (Latin Square-2AFC)

The effect of the test compounds on the perception of the bitter taste of KCl in prepared food products in humans was evaluated using a "chew and spit" test using a Latin Square-2AFC testing method as follows.

Edible KCl food products ("KCl test food product") were prepared according to the following instructions. 6 cups water were boiled in stainless steel pot to a 'rolling' boil. Once a rolling boil was achieved, 166.5 grams of pasta were added to the boiling water. The pasta was stirred briefly to prevent the pasta from sticking to the pot. The pasta was boiled for 8.5 minutes and drained in a stainless steel colander. The pasta was shaken (approximately 15 times back and forth and twice up and down) to remove excess water. The drained pasta was returned to the stainless steel pot, and 56 grams (4 tablespoons) Land O'Lakes™ unsalted butter was added to the hot pasta. When the unsalted butter was half melted, 39.5 grams cheese powder (containing the KCl) was added in the center of the pasta. Separately, test compound was diluted in 1 ml of propylene glycol (PG; alternatively the test compound may also be diluted in a milk stock solution or a butter oil stock solution) and the resulting solution added to 99 ml of milk. 63 ml of the PG/milk solution was poured around cheese powder and gently folded into the pasta with a stainless steel spoon in order to avoid cheese clumping on spoon. KCl standards were similarly prepared by adding milk without any test compound. NaCl standards were similarly prepared by adding cheese powder comprising NaCl and milk without any test compound (NaCl standards did not contain any KCl).

The panelists tasted portions by chewing and spitting. In order to eliminate any effects of sample order, a complete Latin Square design was employed so that each possible order of sample presentation was utilized across subjects. Each sample was tested in several discrete taste test experiments. Panelists were asked to rinse with Poland Spring™ water, eat a cracker, and wait about 10 minutes between samples. In each case, the panelists were asked to choose the sample that tasted less bitter. Illustrative results presented in Table 2.

TABLE 2

KCl Latin Square-2AFC Taste Macaroni and Cheese

| Compound No. | Conc. Of KCl in Cheese Powder (Conc. of KCl in Final Prepared Food Product) | Conc. of Compound Tested in ppm (# of panelists discerning decrease in bitter taste/ # of panelists tested) | Conc. at Which At Least 50% of Panelists Discerned Decrease in Bitter Taste (ppm) | Conc. at Which At Least 50% of Panelists Discerned Decrease in Bitter Taste and p ≤ 0.1 (ppm) |
|---|---|---|---|---|
| 5 | 5.7% (0.34%) | 10 (28/50) 20 (20/49) | 10 | |
| Standard | 5.7% (0.34%) | | | |

We claim:

1. A composition comprising i) a bitter tastant, wherein the bitter tastant is selected from KCl and potassium lactate and ii) a compound according to Formula (I):

Formula (I)

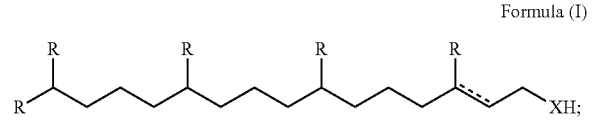

or an enantiomer or diastereomer thereof,
wherein:
X is S or O;
each R is independently H, $C_1$-$C_6$ alkyl, $C_2$-$C_6$ alkenyl, or $C_2$-$C_6$ alkynyl;
wherein the dotted bond indicates an E or Z double bond; or a combination of any of the foregoing compounds, and wherein the compound according to Formula (I) is present in an amount effective to reduce the composition is edible and wherein the bitter taste of the bitter tastant.

2. The composition according to claim 1, wherein said compound is selected from:

Compound 1

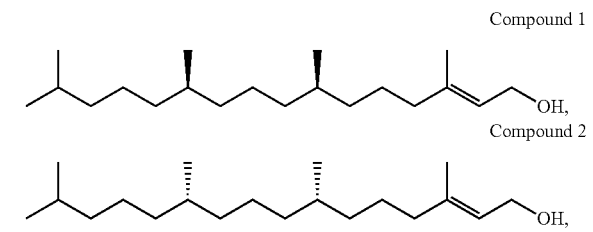

Compound 3

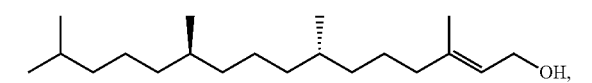

Compound 4

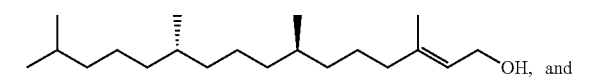

Compound 5

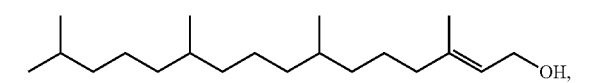

or an enantiomer or diastereomer thereof, or a combination of any of the foregoing compounds.

3. The composition of claim 1 or 2, wherein the composition further comprises one or more component selected from the group consisting of: NaCl and sodium lactate.

4. The composition as defined in claim 1 or claim 2, wherein the composition further comprises a pharmaceutically active ingredient.

5. A method of reducing the bitter taste due to a bitter tastant selected from KCl and potassium lactate, wherein the method comprises placing an edible composition as defined in claim 1 or claim 2 in the oral cavity of a subject.

6. The method of claim 5 wherein the bitter tastant is potassium lactate.

7. The method of claim 5, wherein the edible composition is selected from the group consisting of a food product, a consumer product, and a pharmaceutical composition.

* * * * *